United States Patent
Serrano Carmona et al.

(10) Patent No.: US 10,149,979 B2
(45) Date of Patent: Dec. 11, 2018

(54) SYSTEM TO ESTIMATE THE LOCATION OF A SPINAL CORD PHYSIOLOGICAL MIDLINE

(71) Applicant: Boston Scientific Neuromodulation Corporation, Valencia, CA (US)

(72) Inventors: Raul Serrano Carmona, Los Angeles, CA (US); Bradley Hershey, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 15/467,390

(22) Filed: Mar. 23, 2017

(65) Prior Publication Data

US 2017/0281958 A1    Oct. 5, 2017

Related U.S. Application Data

(60) Provisional application No. 62/317,877, filed on Apr. 4, 2016.

(51) Int. Cl.
*A61N 1/00* (2006.01)
*A61N 1/372* (2006.01)
(Continued)

(52) U.S. Cl.
CPC ........ *A61N 1/37241* (2013.01); *A61B 5/0488* (2013.01); *A61B 5/407* (2013.01);
(Continued)

(58) Field of Classification Search
CPC .... A61B 5/0488; A61B 5/407; A61N 1/0551; A61N 1/36017; A61N 1/36071; A61N 1/36135; A61N 1/37241; A61N 1/37247
See application file for complete search history.

(56) References Cited

U.S. PATENT DOCUMENTS 5,814,092 A    9/1998    King
6,027,456 A    2/2000    Feler et al.
(Continued)

FOREIGN PATENT DOCUMENTS

EP    2703040 A1    3/2014
WO    2006/029090    3/2006

OTHER PUBLICATIONS

International Search Report and Written Opinion regarding PCT Application No. PCT/US2017/024075, dated May 30, 2017.
(Continued)

*Primary Examiner* — George Manuel
(74) *Attorney, Agent, or Firm* — Lewis & Reese, PLLC

(57) ABSTRACT

Techniques for determining the location of a physiological midline are disclosed. A first technique evaluates the response to stimulation of spinal electrodes at peripheral electrodes on different sides of the body. In this technique, a spinal electrode's position relative to a physiological midline is determined based on a relationship between responses to its stimulation observed on different sides of the body. A second technique evaluates the response of spinal electrodes to stimulation of peripheral electrodes on different sides of the body. In this technique, a spinal electrode's position relative to a physiological midline is determined based on the different responses that it observes to stimulation on different sides of the body.

20 Claims, 17 Drawing Sheets

(51) Int. Cl.
*A61N 1/05* (2006.01)
*A61N 1/36* (2006.01)
*A61B 5/0488* (2006.01)
*A61B 5/00* (2006.01)

(52) U.S. Cl.
CPC ....... *A61N 1/0551* (2013.01); *A61N 1/36017* (2013.01); *A61N 1/36071* (2013.01); *A61N 1/36135* (2013.01); *A61N 1/37247* (2013.01)

(56) References Cited

U.S. PATENT DOCUMENTS

| | | | |
|---|---|---|---|
| 6,078,838 | A | 6/2000 | Rubinstein |
| 6,516,227 | B1 | 2/2003 | Meadows et al. |
| 6,718,210 | B1 | 4/2004 | Peckham et al. |
| 6,907,130 | B1 | 6/2005 | Rubinstein et al. |
| 7,890,182 | B2 | 2/2011 | Parramon et al. |
| 8,335,569 | B2 | 12/2012 | Aghassian |
| 8,412,345 | B2 | 4/2013 | Moffitt |
| 8,463,400 | B2 | 6/2013 | Hegi et al. |
| 8,498,716 | B2 | 7/2013 | Chen et al. |
| 8,606,362 | B2 | 12/2013 | He et al. |
| 8,620,436 | B2 | 12/2013 | Parramon et al. |
| 8,768,453 | B2 | 7/2014 | Parramon et al. |
| 8,862,237 | B2 | 10/2014 | Blum et al. |
| 8,913,804 | B2 | 12/2014 | Blum et al. |
| 9,061,140 | B2 | 6/2015 | Shi et al. |
| 9,119,964 | B2 | 9/2015 | Marnfeldt |
| 9,248,279 | B2 | 2/2016 | Chen et al. |
| 2006/0195159 | A1 | 8/2006 | Bradley et al. |
| 2007/0239228 | A1 | 10/2007 | Bradley |
| 2010/0305660 | A1* | 12/2010 | Hegi ................. A61N 1/36071 607/60 |
| 2011/0093030 | A1 | 4/2011 | Goetz et al. |
| 2012/0095529 | A1 | 4/2012 | Parramon et al. |
| 2013/0079848 | A1 | 3/2013 | Campbell et al. |
| 2014/0214131 | A1 | 7/2014 | Bradley |
| 2014/0371819 | A1 | 12/2014 | Goetz et al. |
| 2015/0012061 | A1 | 1/2015 | Chen |
| 2015/0080982 | A1 | 3/2015 | Van Funderburk |
| 2015/0360038 | A1 | 12/2015 | Zottola et al. |

OTHER PUBLICATIONS

U.S. Appl. No. 62/317,884, Serrano Carmona et al., filed Apr. 4, 2016.
U.S. Appl. No. 62/324,801, Hershey et al., filed Apr. 19, 2016.
H. Mino & J. Rubenstein, "Effects of Neural Refractoriness on Spatio-Temporal Variability in Spike Initiations with Eletrical Stimulation," IEEE Trans. On Neural Sys. & Rehabilitation Eng., vol. 14, No. 3, pp. 273-280 (2006).
M. Moffit et al., A Novel 3-Dimensional Algorithm for Model-Based Programming in Spinal Cord Stimulation (SCS): Illumina-3D™, presentation (2013).
M. Hughes, "Fundamentals of Clinical ECAP Measures in Cochlear Implants: Part 1: Use of the ECAP in Speech Processor Programming (2nd Ed.)," Audiology Online (Nov. 8, 2010) (http://www.audiologyonline.com/articles/fundamentalsclinicalecapmeasuresin846).
I. Akhoun et al., "Electrically evoked compound action potential artifact rejection by independent component analysis: Technique validation," Hearing Research 302, pp. 60-73 (2013).
J. Rubinstein et al., "Pseudospontaneous activity: stochastic independence of auditory nerve fibers with electrical stimulation," Hear Res., 127(1-2), pp. 108-118 (1999) (abstract only).
J. Paz, "Physiological Midline Mapping Based on Spinal Cord Stimulation (SCS) Response Using the 32-Contact Paddle Lead," $19^{th}$ NANS Annual Meeting (Dec. 13-15, 2015).
E.L. Air et al., "Electrophysiologic Monitoring for Placement of Laminectomy Leads for Spinal Cord Stimulation Under General Anesthesia," Neuromodulation: Technology at the Neural Interface, vol. 15(6), pp. 573-580 (2012).
J.L. Shils et al., "Intraoperative Neurophysiologic Methods for Spinal Cord Stimulator Placement Under General Anesthesia," Neuromodulation: Technology at the Neural Interface, vol. 15(6), pp. 560-572 (2012).
A. Taghva et al., "Intraoperative Electromyography as an Adjunct to Sacral Neuromodulation for Chronic Pelvic Pain," Neuromodulation: Technology at the Neural Interface, vol. 18(1), pp. 62-66 (2015).

* cited by examiner

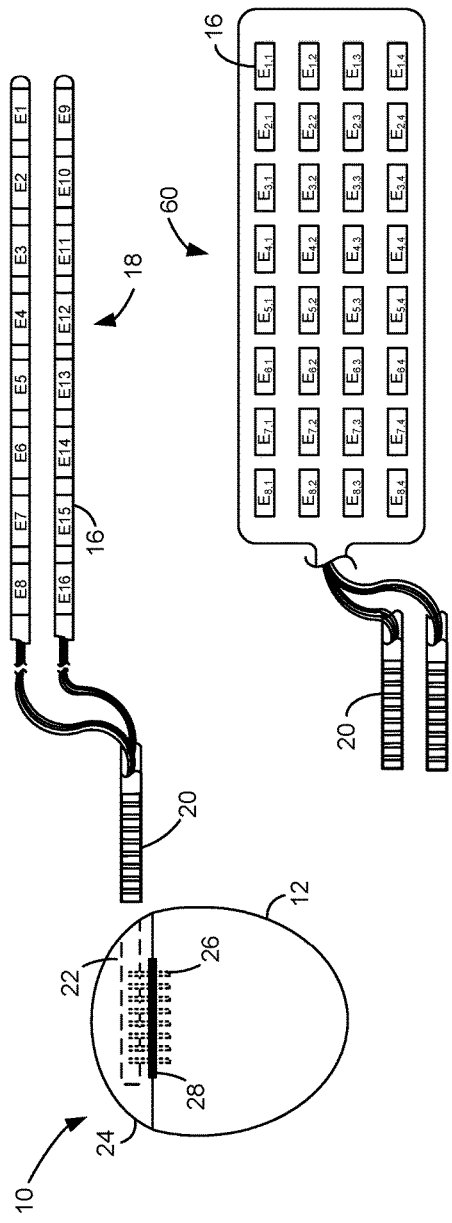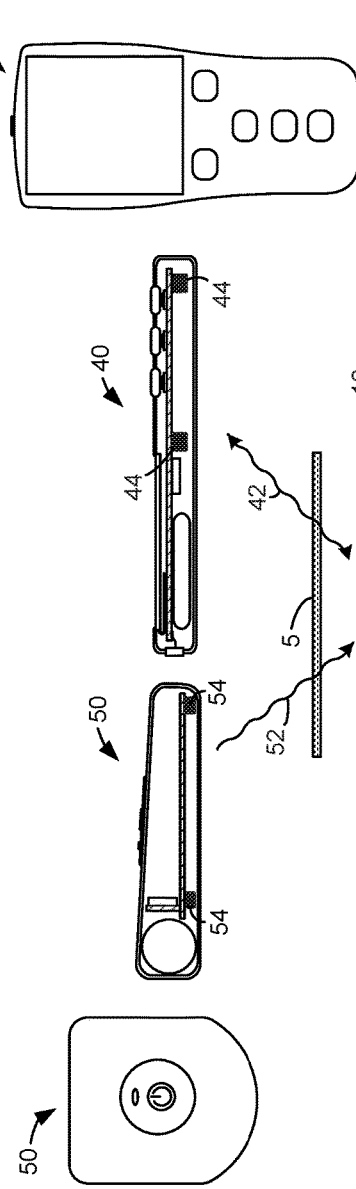
*Figure 1 (prior art)*
*Figure 2 (prior art)*

SYSTEM TO ESTIMATE THE LOCATION OF A SPINAL CORD PHYSIOLOGICAL MIDLINE

CROSS-REFERENCE TO RELTED APPLICATIONS

This is a non-provisional of U.S. Provisional Patent Application Ser. No. 62/317,877, filed Apr. 4, 2016, to which priority is claimed, and which is incorporated herein by reference in its entirety.

This application is also related to U.S. Provisional Patent Application Ser. No. 62/317,884, filed Apr. 4, 2016.

FIELD OF THE TECHNOLOGY

The present application relates to techniques to identify the location of a spinal cord physiological midline, which location can assist in the customization of spinal cord stimulation therapy and/or the evaluation of the suitability of electrode lead placement.

INTRODUCTION

Implantable stimulation devices deliver electrical stimuli to nerves and tissues for the therapy of various biological disorders. The present application is related to a technique to improve the treatment of chronic pain using a Spinal Cord Stimulation (SCS) system. As shown in FIG. 1, a traditional SCS system includes an Implantable Pulse Generator (IPG) 10, which includes a biocompatible device case 12 formed of titanium, for example. The case 12 typically holds the circuitry and battery 14 (FIG. 2) necessary for the IPG 10 to function, which battery 14 may be either rechargeable or primary in nature. The IPG 10 delivers electrical stimulation to a patient's nerves and tissues through electrodes 16, which, in a SCS system are typically positioned within the epidural space within the spinal column. Common electrode arrangements include a linear arrangement along a percutaneous lead 18 and a two-dimensional arrangement on a paddle lead 60. The proximal ends of the leads 18 and 60 include electrode terminals 20 that are coupled to the IPG 10 at one or more connector blocks 22 fixed in a header 24, which can comprise an epoxy, for example. Contacts in the connector blocks 22 make contact with the electrode terminals 20, and communicate with the circuitry inside the case 12 via feedthrough pins 26 passing through a hermetic feedthrough 28 to allow such circuitry to provide stimulation to or monitor the various electrodes 16. The number and arrangement of electrodes on a percutaneous lead 18 or a paddle lead 60 can vary. When percutaneous leads 18 are employed, it is common for two such leads 18 to be implanted with one each on the right and left side of the spinal cord.

As shown in FIG. 2, IPG 10 contains a charging coil 30 for wireless charging of the IPG's battery 14 using an external charger 50, assuming that battery 14 is a rechargeable battery. If IPG 10 has a non-rechargeable (primary) battery 14, charging coil 30 in the IPG 10 and the external charger 50 can be dispensed with. IPG 10 also contains a telemetry coil antenna 32 for wirelessly communicating data with an external controller device 40, which is explained further below. In other examples, antenna 32 can comprise a short-range RF antenna such as a slot, patch, or wire antenna. IPG 10 also contains control circuitry such as a microcontroller 34, and one or more Application Specific Integrated Circuit (ASICs) 36, which can be as described for example in U.S. Pat. No. 8,768,453. ASIC(s) 36 can include stimulation circuitry for providing stimulation pulses at one or more of the electrodes 16 and may also include telemetry modulation and demodulation circuitry for enabling bidirectional wireless communications at antenna 32, battery charging and protection circuitry coupleable to charging coil 30, DC-blocking capacitors in each of the current paths proceeding to the electrodes 16, etc. Components within the case 12 are integrated via a printed circuit board (PCB) 38.

FIG. 2 further shows the external components referenced above, which may be used to communicate with the IPG 10, in plan and cross section views. External controller 40 may be used to control and monitor the IPG 10 via a bidirectional wireless communication link 42 passing through a patient's tissue 5. For example, the external controller 40 may be used to provide or adjust a stimulation program for the IPG 10 to execute that provides stimulation to the patient. The stimulation program may specify a number of stimulation parameters, such as which electrodes are selected for stimulation; whether such active electrodes are to act as anodes or cathodes; and the amplitude (e.g., current), frequency, and duration of stimulation at the active electrodes, assuming such stimulation comprises stimulation pulses as is typical.

Communication on link 42 can occur via magnetic inductive coupling between a coil antenna 44 in the external controller 40 and the IPG 10's telemetry coil 32 as is well known. Typically, the magnetic field comprising link 42 is modulated, for example via Frequency Shift Keying (FSK) or the like, to encode transmitted data. For example, data telemetry via FSK can occur around a center frequency of fc=125 kHz, with a 129 kHz signal representing transmission of a logic '1' bit and a 121 kHz signal representing a logic '0' bit. However, transcutaneous communications on link 42 need not be by magnetic induction, and may comprise short-range RF telemetry (e.g., Bluetooth, WiFi, Zigbee, MICS, etc.) if antennas 44 and 32 and their associated communication circuitry are so configured. The external controller 40 is generally similar to a cell phone and includes a hand-holdable, portable housing.

External charger 50 provides power to recharge the IPG's battery 14 should that battery be rechargeable. Such power transfer occurs by energizing a charging coil 54 in the external charger 50, which produces a magnetic field comprising transcutaneous link 52, which may occur with a different frequency ($f_2$=80 kHz) than data communications on link 42. This magnetic field 52 energizes the charging coil 30 in the IPG 10, which is rectified, filtered, and used to recharge the battery 14. Link 52, like link 42, can be bidirectional to allow the IPG 10 to report status information back to the external charger 50, such as by using Load Shift Keying as is well-known. For example, once circuitry in the IPG 10 detects that the battery 14 is fully charged, it can cause charging coil 30 to signal that fact back to the external charger 50 so that charging can cease. Like the external controller 40, external charger 50 generally comprises a hand-holdable and portable housing.

External controller 40 and external charger 50 are described in further detail in U.S. Patent Application Publication 2015/0080982. Note also that the external controller 40 and external charger 50 can be partially or fully integrated into a single external system, such as disclosed in U.S. Pat. Nos. 8,335,569 and 8,498,716.

As mentioned above, the electrical stimulation that the IPG 10 is capable of delivering is highly customizable with respect to selected electrodes, electrode current amplitude and polarity, pulse duration, pulse frequency, etc. Due to uncertainties in the location of electrodes with respect to neural targets, the physiological response of a patient to stimulation patterns, and the nature of the electrical environment within which the electrodes are positioned, it is essentially impossible to determine the stimulation parameters that might provide effective stimulation therapy for a particular patient prior to implementing stimulation therapy. Thus, in order to determine whether the IPG 10 is capable of delivering effective therapy, and, if so, the stimulation parameters that define such effective therapy, the patient's response to different stimulation parameters is typically evaluated during a trial stimulation phase prior to the permanent implantation of the IPG 10.

As shown in FIG. 3, during the trial stimulation phase, the distal ends of the lead(s) (two percutaneous leads 18 are shown) are implanted within the epidural space 302 along the spinal cord 304 while the proximal ends of the lead(s), including the electrode terminals 20, are ultimately coupled to an external trial stimulator (ETS) 70, which, as its name implies, is external to (i.e., not implanted in) the patient. An external cable box assembly 340 is used to facilitate the connection between the lead(s) and the ETS 70. Each external cable box assembly 340 includes an external cable box 342 (which has a receptacle similar to connector block 22 for receiving the lead), a trial stimulation cable 344, and a male connector 346, which is plugged into a port 72 of the ETS 70.

The ETS 70 essentially mimics operation of the IPG 10 to provide stimulation to the implanted electrodes 16. This allows the effectiveness of stimulation therapy to be verified for the patient, such as whether therapy has alleviated the patient's symptoms (e.g., pain). Trial stimulation using the ETS 70 further allows for the determination of a particular stimulation program that seems promising for the patient to use once the IPG 10 is later implanted into the patient.

Referring to FIG. 4, the stimulation program executed by the ETS 70 can be provided or adjusted via a wired or wireless link (wireless link 92 shown) from a clinician programmer 90, which includes features (described below) that enable a clinician to hone in on the appropriate stimulation therapy settings. As shown, CP system 90 can comprise a computing device 91, such as a desktop, laptop, or notebook computer, a tablet, a mobile smart phone, a Personal Data Assistant (PDA)-type mobile computing device, etc. (hereinafter "CP computer"). In FIG. 4, CP computer 91 is shown as a laptop computer that includes typical computer user interface means such as a screen 92, a mouse, a keyboard, speakers, a stylus, a printer, etc., not all of which are shown for convenience.

Also shown in FIG. 4 are accessory devices for the CP system 90 that are usually specific to its operation as an IPG/ETS controller, such as a communication head 97, and a joystick 98, which are coupleable to suitable ports on the CP computer 91, such as USB ports 99, for example.

Communication between the CP system 90 and the ETS 70 may comprise magnetic inductive or short-range RF telemetry schemes as already described, and in this regard the ETS 70 and the CP computer 91 and/or the communication head 97 (which can be placed proximate to the ETS 70) may include antennas compliant with the telemetry means chosen. For example, the communication head 97 can include a coil antenna 96a, a short-range RF antenna 96b, or both. The CP computer 91 may also communicate directly with the ETS 70, for example using an integral short-range RF antenna 96b.

If the CP system 90 includes a short-range RF antenna (either in CP computer 91 or communication head 97), such antenna can also be used to establish communication between the CP system 90 and other devices, and ultimately to larger communication networks such as the Internet. The CP system 90 can typically also communicate with such other networks via a wired link 95 provided at a Ethernet or network port 93 on the CP computer 91, or with other devices or networks using other wired connections (e.g., at USB ports 99).

Joystick 98 is generally used as an input device to select various stimulation parameters (and thus may be redundant of other input devices to the CP computer 91), but is also particularly useful in steering currents between electrodes to arrive at an optimal stimulation program, as discussed further below.

To program stimulation parameters, the clinician interfaces with a clinician programmer graphical user interface (CP GUI) 94 provided on the display 92 of the CP computer 91. As one skilled in the art understands, the CP GUI 94 can be rendered by execution of CP software 100 on the CP computer 91, which software may be stored in the CP computer's non-volatile memory 98. Such non-volatile memory 98 may include one or more non-transitory computer-readable storage mediums including, for example, magnetic disks (fixed, floppy, and removable) and tape, optical media such as CD-ROMs and digital video disks (DVDs), and semiconductor memory devices such as Electrically Programmable Read-Only Memory (EPROM), Electrically Erasable Programmable Read-Only Memory (EEPROM), and USB or thumb drive. One skilled in the art will additionally recognize that execution of the CP software 100 in the CP computer 91 can be facilitated by control circuitry 89 such as a microprocessor, microcomputer, an FPGA, other digital logic structures, etc., which is capable of executing programs in a computing device. Such control circuitry 89 when executing the CP software 100 will in addition to rendering the CP GUI 94 enable communications with the ETS 70 through a suitable antenna 96a or 96b, either in the communication head 97 or the CP computer 91 as explained earlier, so that the clinician can use the CP GUI 94 to communicate the stimulation parameters to the ETS 70.

An example of a portion of the CP GUI 94 is shown in FIG. 5. The illustrated portion of the GUI 94 includes fluoroscopic image 502, which shows the implanted leads relative to anatomical structures, such as vertebrae. Using the illustrated interface, a user can select a representation 506 of the implanted electrode lead from left side panel 504, which includes representations 506 of various types of lead products such as 1×8 percutaneous lead representation 506A, 1×16 percutaneous lead representation 506B, and 4×8 paddle lead representation 506C. The user can then drag the selected lead representation 506 onto the fluoroscopic image 502 and manipulate its size and orientation until it aligns with the implanted electrode lead in the image 502. Because the representations 506 are programmed with properties of the lead such as electrode size, shape, and spacing, the positioning of a lead representation 506 on the fluoroscopic image 502 relates the locations of the electrodes to the image 502. This enables a user to subsequently visualize through the GUI 94 the anatomical location of a centroid of electrical stimulation. For example, based on the known location of a particular first stimulating cathode 508A on the lead corresponding to the representation 506A$_1$ and the known location of a particular second stimulating cathode 508B on the lead corresponding to the representation 506A$_2$, as well as the stimulation parameters of the first and second cathodes (e.g., relative amplitudes), the location of the centroid of cathodic stimulation 510 can be depicted over the fluoroscopic image 502. This enables the user to visualize the anatomic location of cathodic stimulation.

Such anatomical visualization of electrical stimulation can be beneficial in determining the desired stimulation program due to the spatial relationship between the point of stimulation and the location at which the effect of stimulation is perceived by a patient. While the precise mechanism by which spinal cord stimulation interrupts the sensation of pain is not fully understood, it is understood that the stimulation of a spinal nerve on a particular side of a patient's body results in the perception of stimulation (or simply the interruption of what was previously perceived as pain) on the same side of the body. For example, pain in the upper right leg, which is perceived as a result of the transmission of a neurological signal through sensory neurons from the location of the pain through a spinal nerve on the same side of the body and into the spinal cord where it is further transmitted to the brain, is interrupted by the application of electrical stimulation to the spinal nerve through which the pain signal travels (i.e., the spinal nerve on the right side of the body). Therefore, the visualization of the anatomical point of stimulation provides information that can guide the user in determining the appropriate stimulation parameters to treat a patient's particular pain symptoms.

The inventors have determined, however, that the anatomical location of a point of stimulation does not provide a full understanding of the probable effects of stimulation. This is because the neuroanatomy is not necessarily aligned with the anatomical features that are visible in an image such as fluoroscopic image 502. For example, the physiological midline may deviate from the anatomical midline to some extent. These shortcomings have prompted the inventors to develop a technique for identifying and providing additional information that can be utilized in the determination of stimulation parameters that may be effective for a particular patient as well as information that can be utilized in evaluating the suitability of lead placement.

BRIEF DESCRIPTION OF THE DRAWINGS

FIG. 1 shows an implantable pulse generator (IPG), in accordance with the prior art.

FIG. 2 shows a cross section of the IPG of FIG. 1 as implanted in a patient, as well as external devices that support the IPG, including an external charger and external controller, in accordance with the prior art.

DETAILED DESCRIPTION

Figure 6:
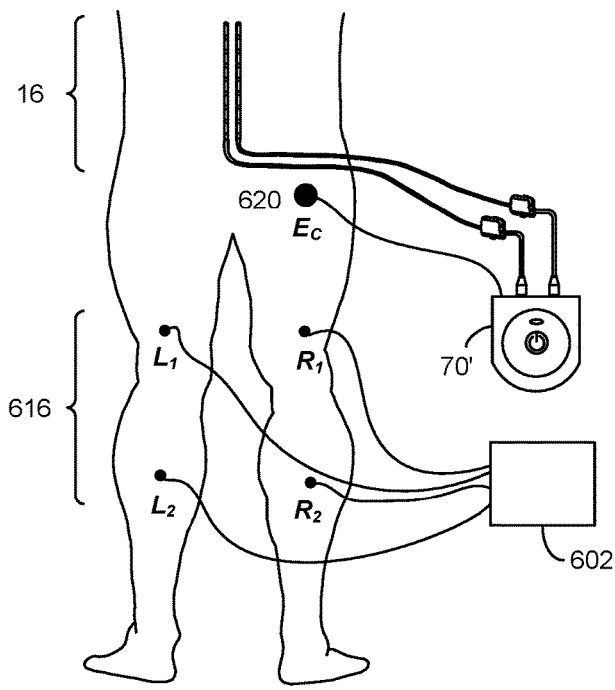
FIG. 6 shows the connection of spinal and peripheral electrodes to an external trial stimulator and a monitoring electrode device for determining the location of a physiological midline, in accordance with an example of the invention.

Given the above-noted shortcomings of the use of anatomical features to guide the determination of stimulation parameters and verify the suitability of electrode lead placement, the inventors disclose a technique for identifying and presenting the location of a physiological midline with respect to implanted electrodes. Referring to FIG. 6, a first aspect of the invention employs peripheral electrodes 616 (labeled $L_1$, $L_2$, $R_1$, and $R_2$) in conjunction with spinal electrodes 16 on one or more implanted electrode leads (such as leads 18 or 60) to determine the location of the physiological midline of a patient based on the peripheral response to spinal stimulation at different electrodes 16. As used herein, a peripheral electrode is an electrode positioned at a location of a patient other than the patient's spinal column that can measure an electrical response to stimulation of a spinal electrode or induce a response (via electrical stimulation of the peripheral electrode) that is observable at a spinal electrode. Four electromyography (EMG) peripheral electrodes 616 are shown in FIG. 6, but more or fewer electrodes may also be employed. The EMG peripheral electrodes 616 may be surface electrodes (which measure electrical activity produced by skeletal muscles through the skin) or intramuscular electrodes (which are inserted through the skin into the muscle tissue to measure the electrical activity of the muscle). While the description of this first aspect of the invention focuses on the use of EMG peripheral electrodes 616, different types of biosignals that can be evaluated at known lateral positions (i.e., right or left) can also be employed. For example, electroencephalography (EEG) electrodes such as surface electrodes placed on the face and scalp can also be utilized. Moreover, while EMG electrodes are depicted as being placed in or on different leg muscles, the peripheral monitoring electrodes may be placed at any peripheral muscle locations having a known lateral position.

The disclosed technique operates on the principle that spinal cord stimulation on a particular side of a physiological midline results in the recruitment of a greater number of neurons on the same side of the physiological midline than on the opposite side of the physiological midline, which imbalance is detectable as a difference in electrical activity at corresponding peripheral monitoring electrodes on different sides of the body. For example, in the case of EMG peripheral electrodes, spinal cord stimulation on the right side of the physiological midline results in the recruitment of a greater number of motor neurons on the right side of the physiological midline than on the left side of the physiological midline, which results in muscle activity (e.g., contractions) that is more pronounced on the right side, which is detectable as an EMG signal having a greater amplitude on the right side. Similarly, in the case of EEG electrodes, spinal cord stimulation on a particular side of the physiological midline results in the recruitment of a greater number of sensory neurons on that side of the midline, which is detectable as a higher degree of electrical activity on the same side of the brain.

Because the technique is based upon relative responses on different sides of the body, the monitoring electrodes are preferably arranged in corresponding pairs. For example, if electrode $L_1$ is placed over or in the lower left quadriceps muscle, electrode $R_1$ is preferably placed over or in the lower right quadriceps muscle. Similarly, if electrode $L_2$ is placed over or in the middle of the left gastrocnemius muscle, electrode $R_2$ is preferably placed over or in the middle of the right gastrocnemius muscle.

The peripheral electrodes 616 are coupled to circuitry (described below) within a monitoring electrode device 602 and the spinal electrodes 16 (i.e., the electrodes on the implanted lead(s)) are stimulated by circuitry within a modified ETS 70', which is modified in the sense that it is additionally configured to stimulate a complementary electrode (Ec) 620, the function of which will be described below. Although a modified ETS 70' is shown, the spinal electrodes 16 and the complementary electrode 620 may alternatively be stimulated by a dedicated stimulating device.

Figure 7:
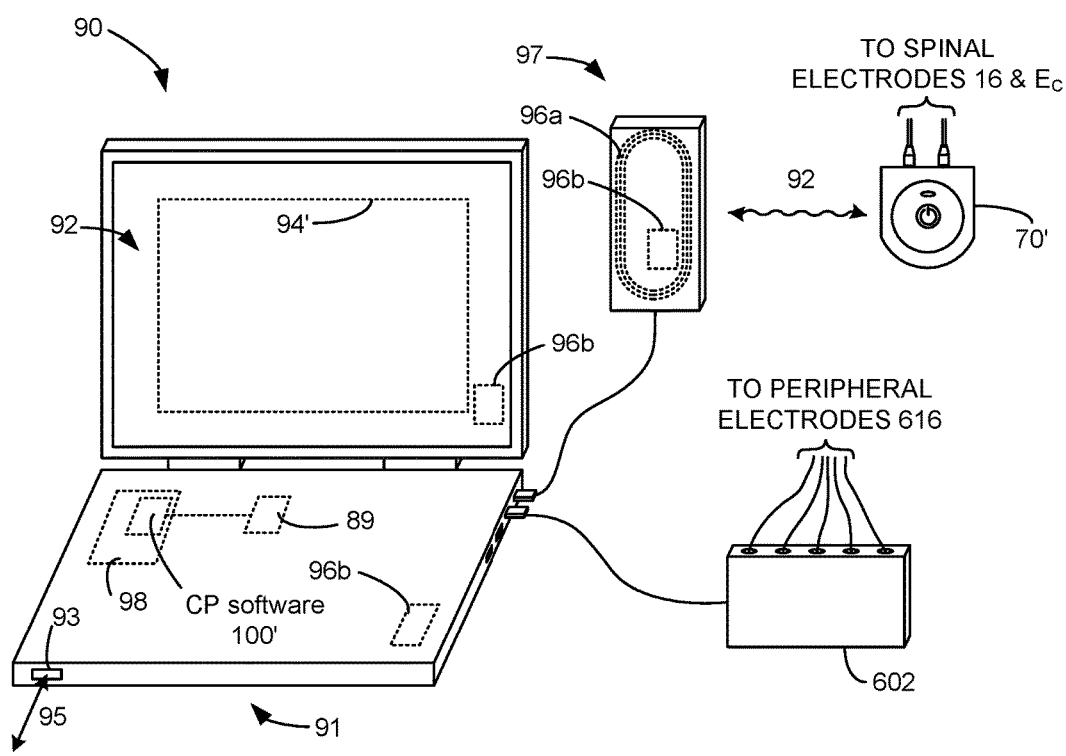
FIG. 7 shows the connection of the external trial stimulator and the monitoring electrode device to a clinician's programmer system, in accordance with an example of the invention.

As illustrated in FIG. 7, the modified ETS 70' and the monitoring electrode device 602 are connected to the CP computer 91. While different wired and wireless connections are shown, the monitoring electrode device 602 and the modified ETS 70' (or the separate dedicated stimulating device) can be connected to the CP computer 91 in any way that allows the relevant commands and data to be passed between the devices. The CP computer 91 executes improved CP software 100', which incorporates physiological midline determination algorithms, as described below, and an improved GUI 94', which enables the presentation of an identified physiological midline.

Figure 8:
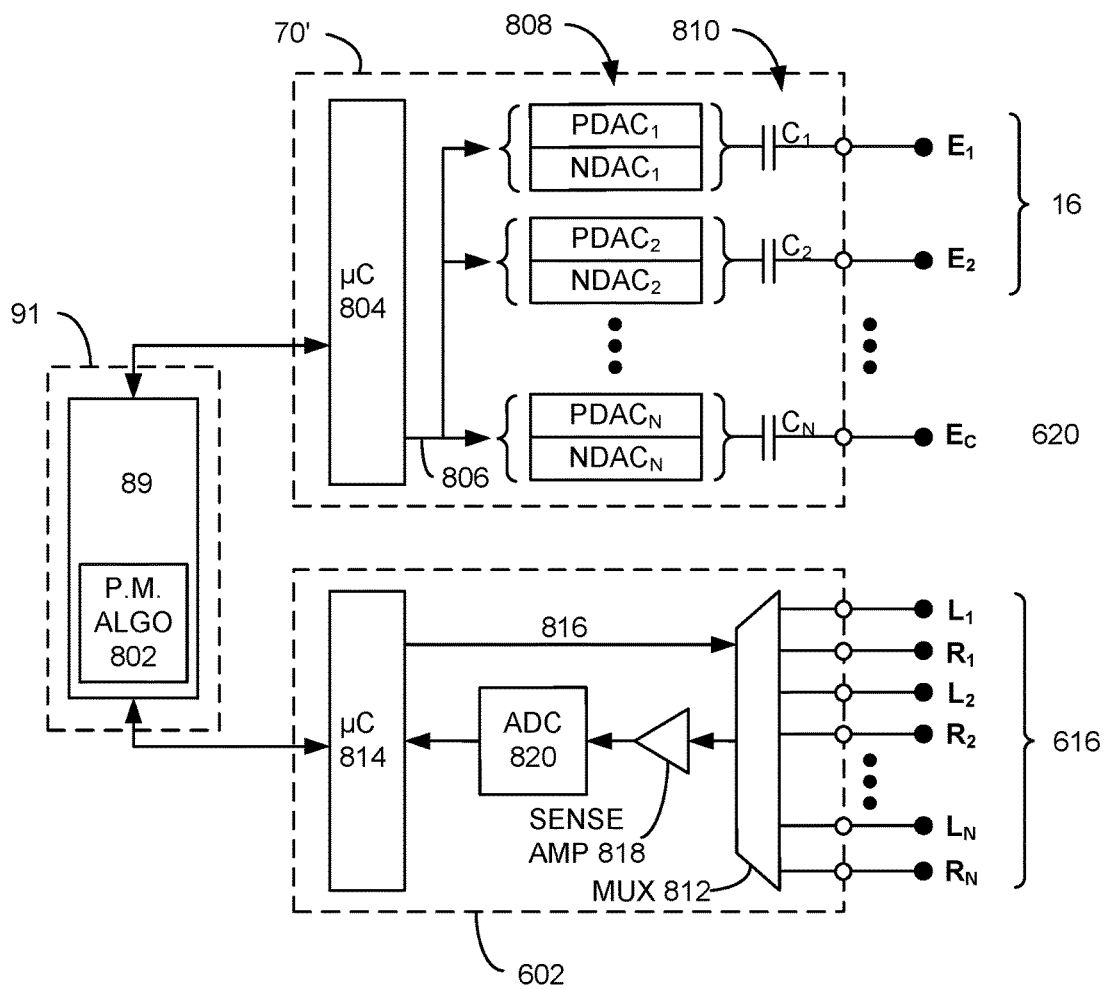
FIG. 8 shows a portion of the circuitry of the external trial stimulator, the monitoring electrode device, and the clinician's programmer, in accordance with an example of the invention.

Referring to FIG. 8, the CP computer 91 includes control circuitry 89 (such as a microcontroller) that communicates with the modified ETS 70' and the monitoring electrode device 602. In particular, the CP computer 91 sends stimulation instructions to the modified ETS 70' and receives data from the monitoring electrode device 602, which instructions and data may be provided and received in accordance with the execution of a physiological midline algorithm 802 by the control circuitry 89.

The modified ETS 70' includes control circuitry 804, which may comprise a microcontroller, or which may be formed in whole or in part in one or more Application Specific Integrated Circuits (ASICs), as described in U.S. Patent Application Publication 2012/0095529 and U.S. Pat. Nos. 9,061,140 and 8,768,453. A bus 806 provides digital control signals to one or more Digital-to-Analog converters (DACs) 808, which are used to produce currents or voltages of prescribed amplitudes (A) for the stimulation pulses, and with the correct timing. As shown, the DACs include both PDACs which source current to a chosen anode electrode, and NDACs which sink current from a chosen cathode electrode. Notice that the current paths to the electrodes include DC-blocking capacitors 810, which as known provide additional safety by preventing the inadvertent supply of DC current to an electrode and to a patient's tissue. Bus 806 thus addresses an appropriate PDAC or NDAC to set the polarity of the stimulation pulses. Although dedicated DACs 808 are shown for each of the spinal electrodes 16 and the complementary electrode 620, fewer DACs 808 may also be employed through the implementation of a switch matrix between the DACs 808 and the electrodes. The illustrated circuitry for producing stimulation pulses and delivering them to the electrodes is merely one example. Other approaches may be found for example in U.S. Pat. Nos. 8,606,362 and 8,620,436.

The peripheral electrodes 616 are each coupled to a multiplexer 812 in the monitoring electrode device 602. The multiplexer 812 passes the signal from one of the peripheral electrodes 616 to a sense amp 818 based on a signal it receives from the control circuitry 814 (which may comprise a microcontroller) over the bus 816. Although not shown, level shift circuitry may be implemented between the multiplexer 812 and the sense amp 818 to shift the magnitude of the signal into the middle of the operating range of the sense amp 818 as is well known in the art. In addition, the signal may be processed using an anti-aliasing filter (e.g., a band-pass filter) prior to amplification by the sense amp 818. While multiplexer 812 enables the use of a shared sense amp 818, this arrangement is not strictly necessary, and instead each electrode 616 can be coupled to its own dedicated sense amp 818, which beneficially enables parallel processing of the signals from the electrodes 616. The analog waveform received from the electrode 616, as filtered and amplified, is preferably converted to digital signals by an Analog-to-Digital converter 820, which may also reside within the control circuitry 814. Although not illustrated, the monitoring electrode device 602 may include a memory for storing the digitized signals. Like the modified ETS 70', the circuitry in the monitoring electrode device 602 may be formed in whole or in part in one or more ASICs. As will become clear based on the description below, the algorithm 802 must be aware of the lateral position associated with signals it receives from the peripheral electrodes 616. Therefore, the monitoring electrode device 602 may have ports that are marked to indicate the position of the signal that should be routed to that port (i.e., left or right) or the algorithm 802 may enable a user to specify the lateral position associated with the signals routed to different ones of the device 602's ports.

Figure 9:
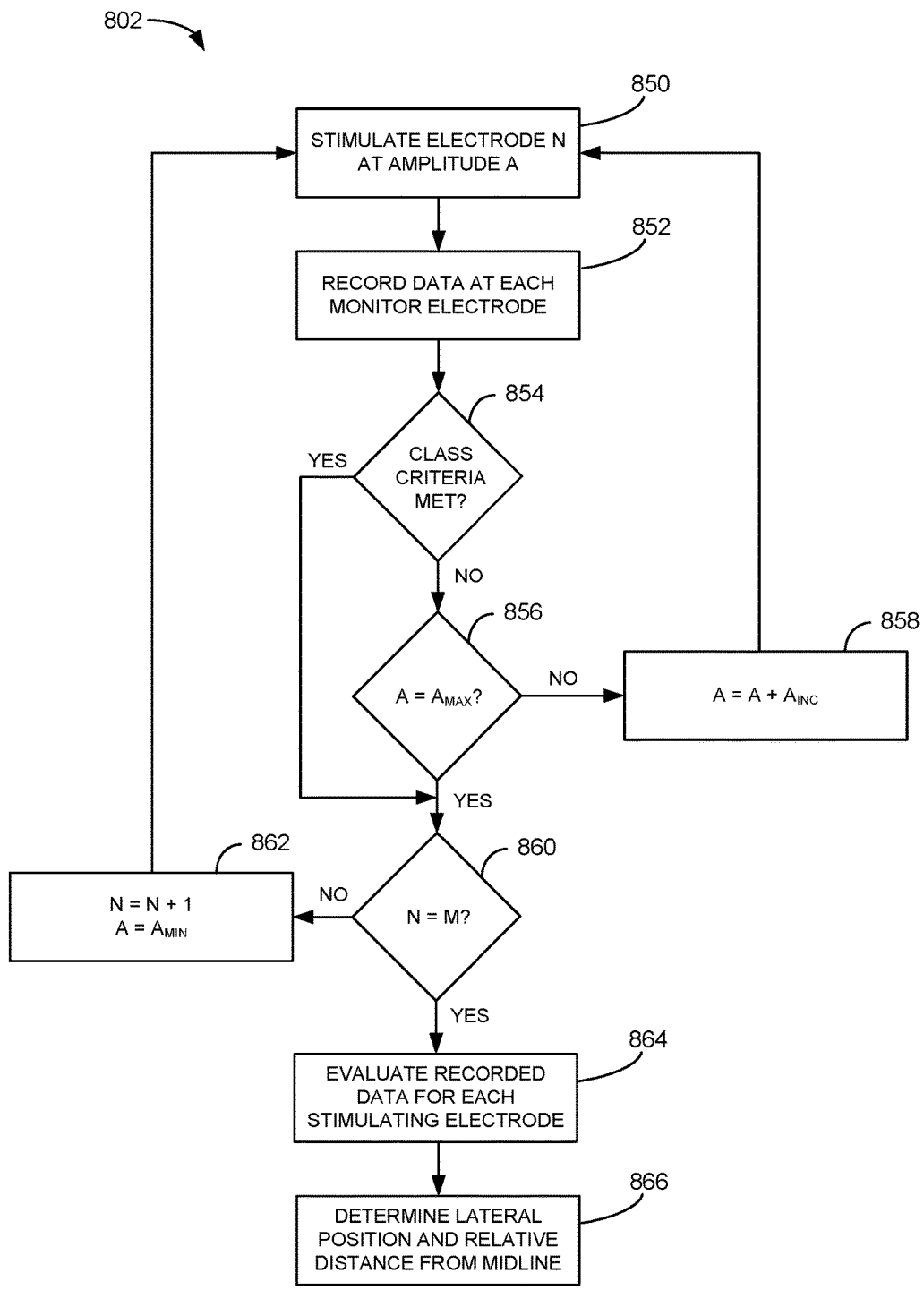
FIG. 9 is a flowchart that shows various steps of a peripheral monitoring physiological midline determination algorithm, in accordance with an example of the invention.

FIG. 9 is a flowchart that illustrates the steps in an example peripheral monitoring physiological midline algorithm 802. The algorithm 802 operates to determine the location of the physiological midline by stimulating various spinal electrodes 16 and observing the response at peripheral electrodes 616 at different lateral positions. Initially, the electrode number (N) is set equal to 1 and the amplitude (A) is set equal to a minimum value ($A_{min}$) (e.g., a minimum current value of 5 mA). The minimum amplitude value may be a customizable parameter of the algorithm 802 that is selectable via the user interface 94', for example. It should be noted that the stimulation levels required to recruit motor neurons may be significantly higher than typical SCS stimulation levels, so, when the algorithm 802 is executed with EMG peripheral electrodes 616, the minimum amplitude level may be set at a relatively high (compared to typical SCS stimulation currents) current level. It is further noted that such stimulation levels, while well below maximum allowable limits, may be uncomfortable for a patient, so a patient may be at least partially sedated during the execution of the algorithm 802.

At step 850, the selected spinal electrode 16 (i.e., electrode N) is stimulated at the selected amplitude. In a preferred embodiment, a single spinal electrode 16 is stimulated in combination with the complementary electrode 620. Specifically, the complementary electrode 620 is stimulated at an equal magnitude and an opposite polarity from the selected spinal electrode 616. The complementary electrode 620 is preferably a surface electrode (i.e., adhered to the patient's skin) having a relatively large area and is positioned remotely from the spinal electrodes 16 as well as from the peripheral electrodes 616. The remote location and the large area of the complementary electrode 620 ensures that its stimulation does not interfere with the signals measured at the peripheral electrodes 616 and that the spinal electrode 16 (which produces a localized field in close proximity to a spinal nerve), and not the complementary electrode 620, is responsible for any observed reaction at the peripheral electrodes 616. Although the use of complementary electrode 620 is described, stimulation may also occur using two or more spinal electrodes 16 that are in close proximity to one another (e.g., neighboring electrodes may serve as an anode and cathode). In fact, as described below, simultaneous stimulation of multiple spinal electrodes 16 can enable greater spatial resolution through the creation of "virtual" electrodes and can additionally enable use of a conventional ETS 70 (i.e., without modification to accommodate the complementary electrode 620). In one embodiment, the selected electrode and the complementary electrode 620 are stimulated using a square waveform having a low frequency of approximately 2-10 Hz. However, the desired stimulation waveform and amplitude may be user-selectable parameters.

During stimulation, the signal at each of the peripheral electrodes 616 is recorded (step 852). As described above with respect to FIG. 8, recording the signals from the monitoring electrode 616 may be performed serially (via multiplexer 812, for example) or in parallel if dedicated sense amps 818 and ADCs 820 are provided for each electrode. Such recording may involve the storage in memory (either in CP system 90 or monitoring electrode device 602) of the digitized values of the signals. Based on the recorded data, it is determined if any classification criteria have been met (step 854). The classification criteria serve to stop stimulation for the selected spinal electrode 16 when enough information has been gathered to make a determination as to the location of the physiological midline with respect to the electrode. A first example classification criterion may limit the number of increased-amplitude stimulation cycles following a detectable response at any peripheral electrode 616 (e.g., stimulation may proceed to a next spinal electrode following two amplitude increases after a response at any peripheral electrode 616 that exceeds a threshold level). A second example classification criterion may cause the algorithm 802 to proceed to a next electrode if bilateral stimulation (e.g., a detectable response that exceeds a threshold level at each of corresponding bilateral electrodes) is observed. Other similar types of classification criteria can also be implemented and, in one embodiment, may be customizable by the user. Although step 852 indicates that data is recorded, it will be understood that some processing of the recorded data must also occur at this stage in order to apply the classification criteria.

If no classification criterion is met, it is determined if the stimulation amplitude is at the maximum level (step 856). The maximum stimulation amplitude ($A_{max}$) may be a user-configurable value that can be set up to a programmed maximum limit, which is safely below allowable limits. If the stimulation amplitude is not equal to the maximum stimulation amplitude, it is increased by an incremental amount ($A_{INC}$), which may also be user-selectable (step 858). For example, if the incremental amount is set to 0.1 mA, the amplitude is increased by 0.1 mA at each cycle. The process then returns to step 850 for stimulation of the same selected electrode at the increased amplitude value.

If, however, either a classification criterion is met or the amplitude is equal to the maximum amplitude, it is determined whether any spinal electrodes 16 remain to be stimulated (i.e., whether the selected electrode (N) is the last electrode (M)) (step 860). For example, if the algorithm 802 is executed in a system having two implanted electrode leads each having 8 electrodes, the last electrode (M) is set to 16. If the selected electrode is not the last electrode, the next electrode is selected and the amplitude is reset to the minimum amplitude (step 862). The process then returns to step 850 for stimulation of the next electrode at the minimum amplitude.

Once the process has proceeded through all of the spinal electrodes 16, the data recorded at the peripheral electrodes 616 is evaluated for each of the spinal electrodes 16 (step 864) and the lateral position (i.e., left or right of physiological midline) and relative distance from the midline is determined for each electrode (step 866). These steps are best described with reference to FIGS. 10 and 11.

Figure 10:
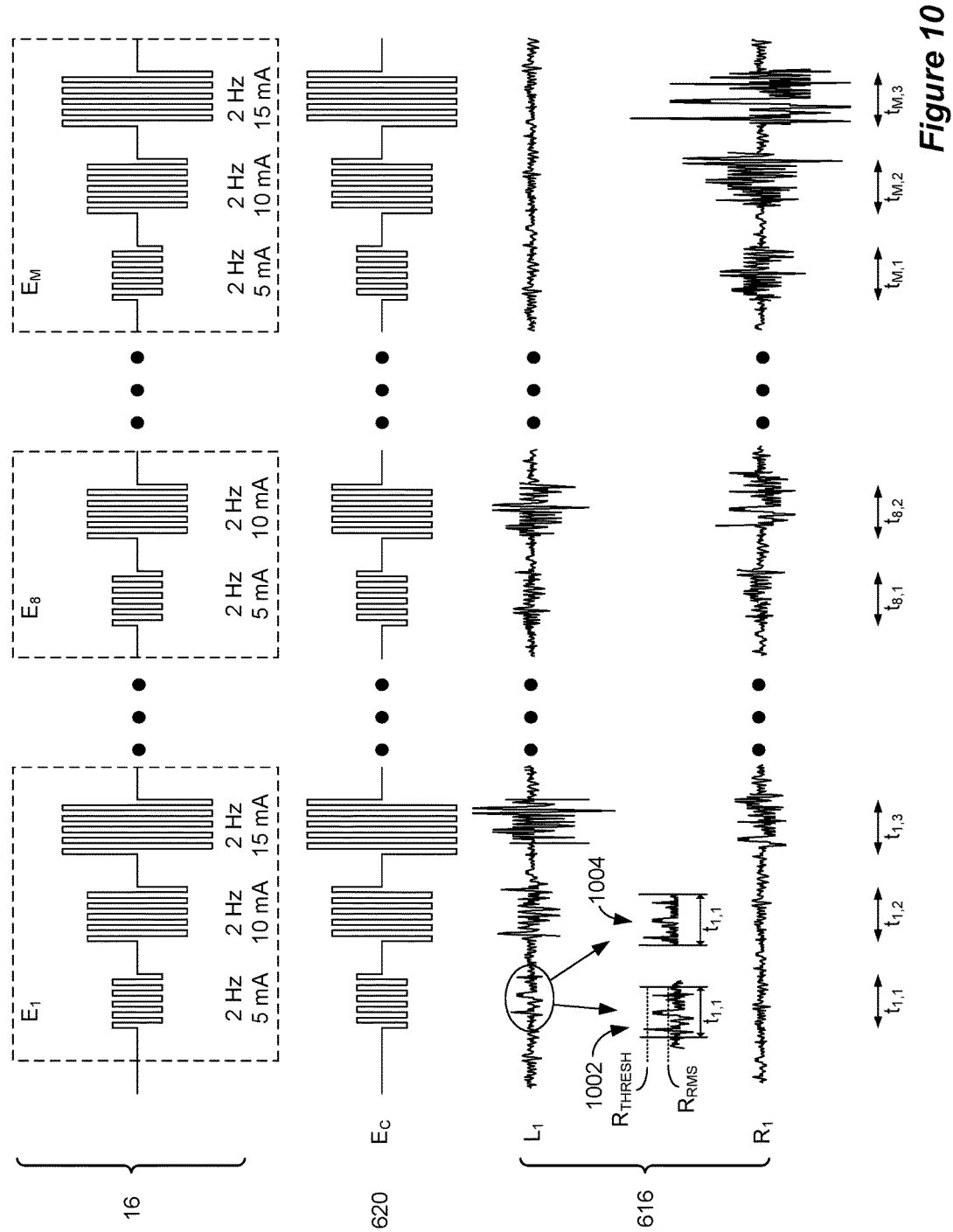
FIG. 10 shows example stimulation patterns and response signals associated with the peripheral monitoring physiological midline determination algorithm, in accordance with an example of the invention.

FIG. 10 illustrates the stimulation pattern at various spinal electrodes 16 and the corresponding electrode 620 as well as the response to such stimulation at peripheral electrodes 616 in an example execution of the algorithm 802. In the example shown, two classification criteria are employed: 1) no more than two additional stimulation cycles may be conducted for a selected spinal electrode 16 after the observance of a super-threshold signal at any peripheral electrode 616 in response to stimulation of the selected spinal electrode 16 and 2) no additional stimulation cycles may be conducted for a selected spinal electrode 16 after the observance of a super-threshold signal at each of a corresponding pair of peripheral electrodes 616 (e.g., $L_1$ and $R_1$, $L_2$ and $R_2$, etc.). While the first classification criterion is expressed in terms of a number of stimulation cycles after an identified event, it may also be expressed in terms of an amplitude limit (e.g., no more than an increase of 2 mA).

Electrode $E_1$ is initially stimulated using a square waveform at a frequency of 2 Hz and an amplitude of 5 mA during a time period $t_{1,1}$. The corresponding electrode 620 is simultaneously stimulated with an equal and opposite stimulation pattern. During stimulation (i.e., during all or some portion of the period $t_{1,1}$), the electrical activity at various peripheral electrodes 616 is observed and recorded. In the example shown, the response of each of a corresponding pair of EMG electrodes ($L_1$ and $R_1$) is recorded. Although a single corresponding pair of peripheral electrodes 616 is shown, additional pairs may be used and evaluated during the same stimulation sequence as described above. Moreover, while an EMG response is shown, peripheral electrodes might also include other types of biosignals (such as EEG signals) having a lateral relationship to spinal stimulation.

The response to stimulation during the time period $t_{i,i}$ is measured at the peripheral electrodes $L_1$ and $R_1$. The response measured at each peripheral electrode 616 can be quantified in different ways such as the root mean square (RMS) of sampled values (1002), the integral of rectified sampled values during a time period (e.g., all or part of a stimulation time period) (1004), or other known statistical measures. Regardless of the manner in which the response is quantified, the quantified value is compared to a threshold value. The threshold value may be selected to be some multiple (e.g., 3×) of the average signal noise. In the example shown, neither the $L_1$ nor the $R_1$ signal response exceeds the threshold level during $t_{1,1}$. Therefore, neither classification criterion is invoked.

The algorithm therefore initiates another stimulation cycle in which $E_1$ and $E_C$ are stimulated at a higher amplitude of 10 mA during a subsequent time period $t_{1,2}$. While a large increase in amplitude (i.e., $A_{INC}=5$ mA) is shown for purposes of illustration, it will be understood that smaller incremental values may be used in an actual implementation. During time period $t_{1,2}$, the response at $L_1$ exceeds the threshold, but the response observed at $R_1$ is still below the threshold. The super-threshold $L_1$ response during $t_{1,2}$ invokes the first classification criterion such that the number of subsequent stimulation cycles is limited to two. $E_1$ and $E_C$ are thereafter stimulated at a further increased amplitude of 15 mA during the time period $t_{1,3}$, which results in a super-threshold response at both $L_1$ and $R_1$. The bilateral response (i.e., the super-threshold response at each of a corresponding pair of peripheral electrodes 616) invokes the second classification criterion such that no additional stimulations of $E_1$ are performed even though the first criterion would allow for one additional stimulation cycle. As a result, the algorithm proceeds to the next spinal electrode $E_2$ and continues sequentially through the electrodes.

Eventually, $E_8$ and $E_C$ are stimulated at 5 mA during a time period $t_{8,1}$ which results in a sub-threshold response at both $L_1$ and $R_1$ and at 10 mA during a time period $t_{8,2}$, which results in a super-threshold response at both $L_1$ and $R_1$. The bilateral response during time period $t_{8,2}$ causes the algorithm 802 to continue through its sequential progression through the spinal electrodes 16 until it reaches last electrode $E_M$. $E_M$ and $E_C$ are stimulated at 5 mA, 10 mA, and 15 mA at time periods $t_{M,1}$, $t_{M,2}$, and $t_{M,3}$, respectively. Each stimulation results in a super-threshold response at $R_1$ and a sub-threshold response at $L_1$. As a result, the stimulation of $E_M$ is terminated based on the first classification criterion without any bilateral response, and the stimulation portion of the algorithm 802 is completed.

Figure 3:
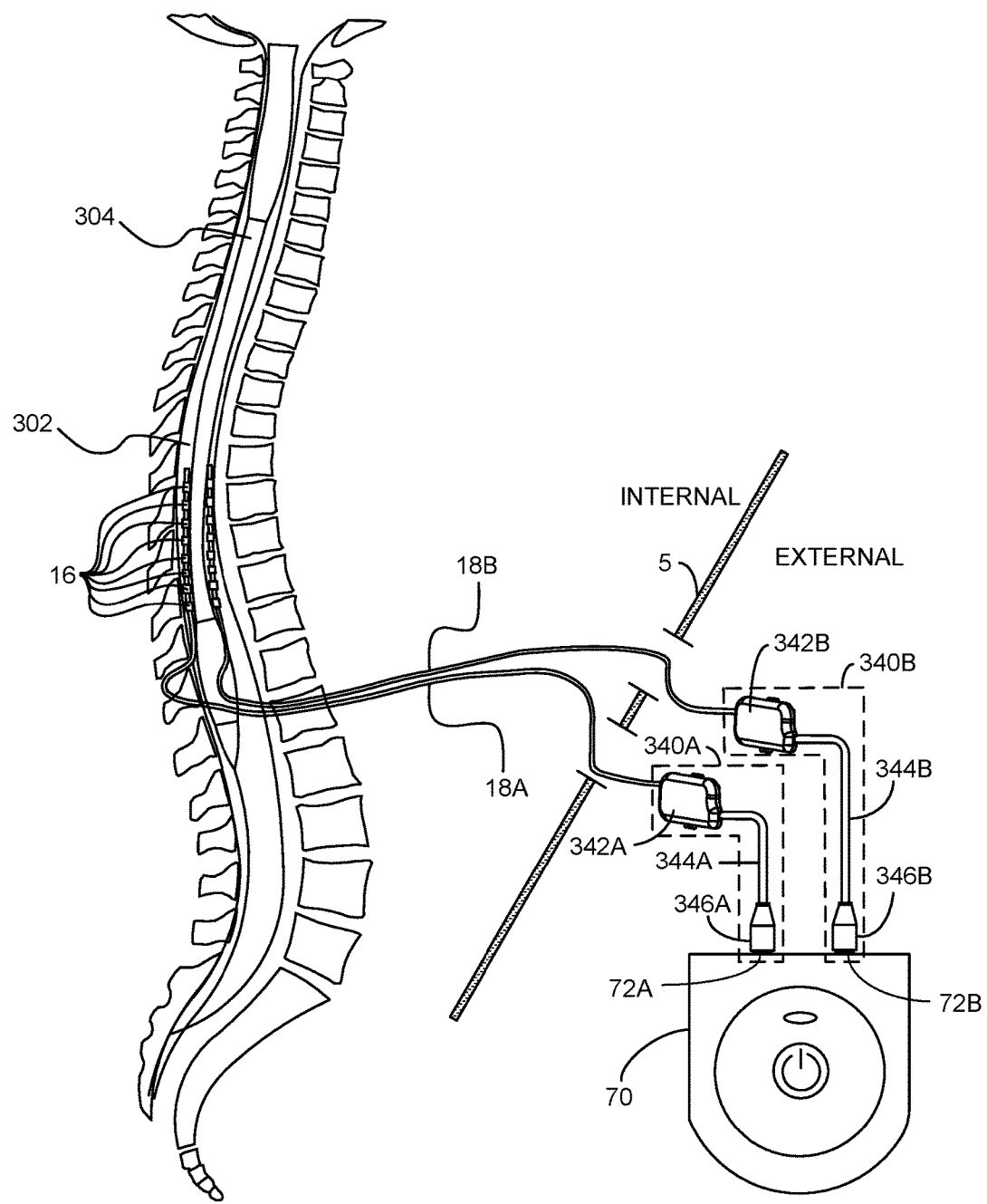
FIG. 3 shows use of trial stimulation preceding implantation of the IPG, including implanted leads/electrodes communicating with an External Trial Stimulator (ETS), in accordance with the prior art.
Figure 4:
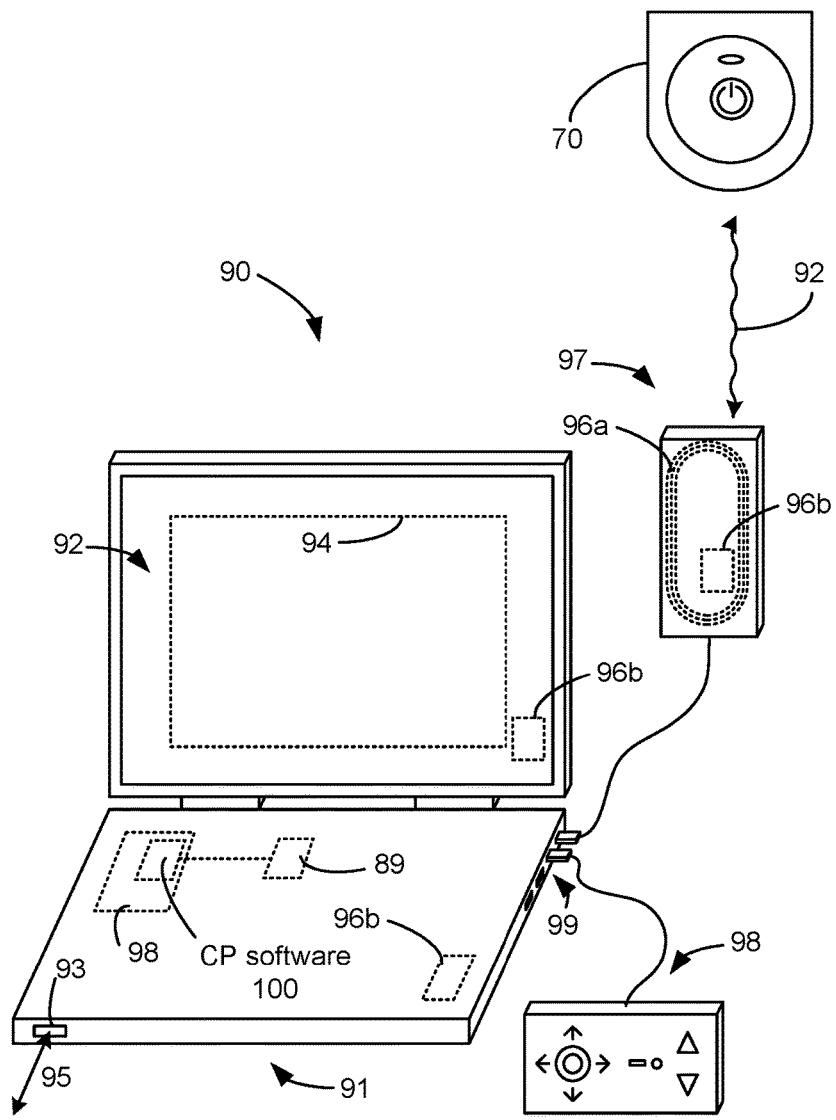
FIG. 4 shows components of a clinician's programmer system, including components for communicating with an external trial stimulator, in accordance with the prior art.
Figure 5:
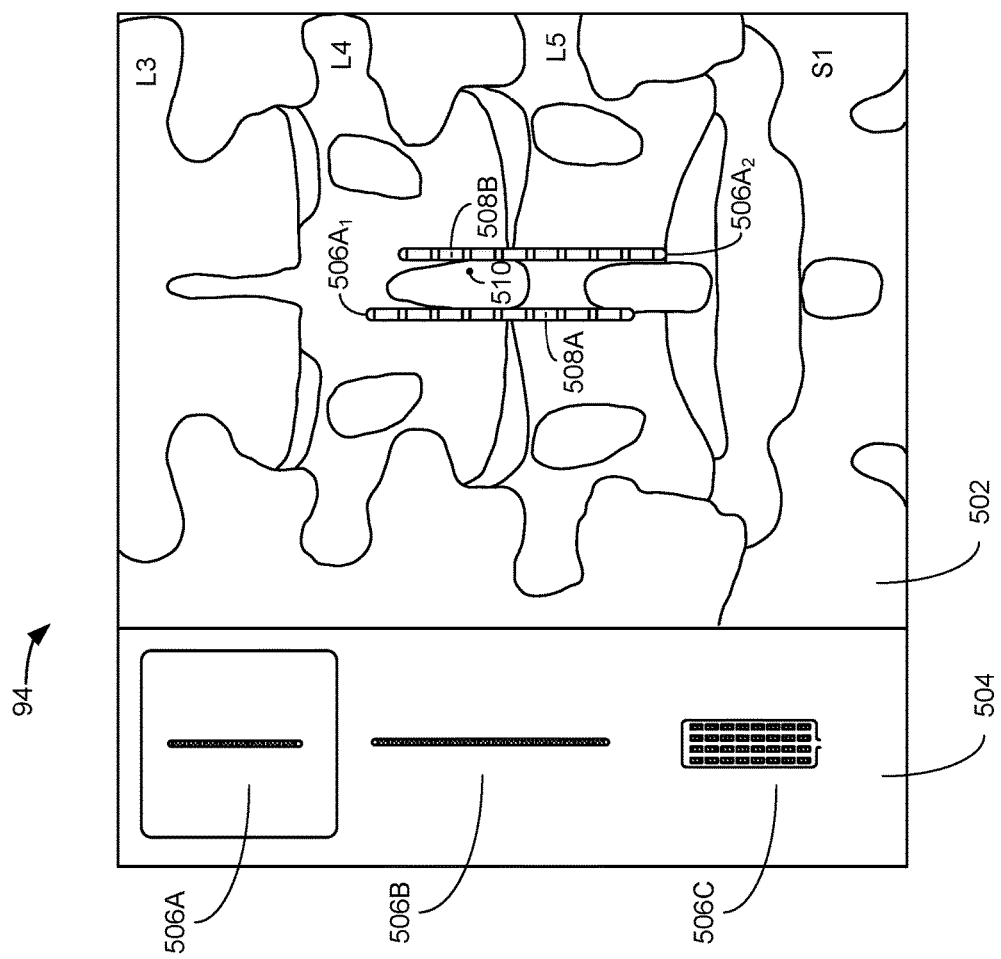
FIG. 5 shows an example of a graphical user interface that can be provided on the clinician's programmer system, in accordance with the prior art.
Figure 11:
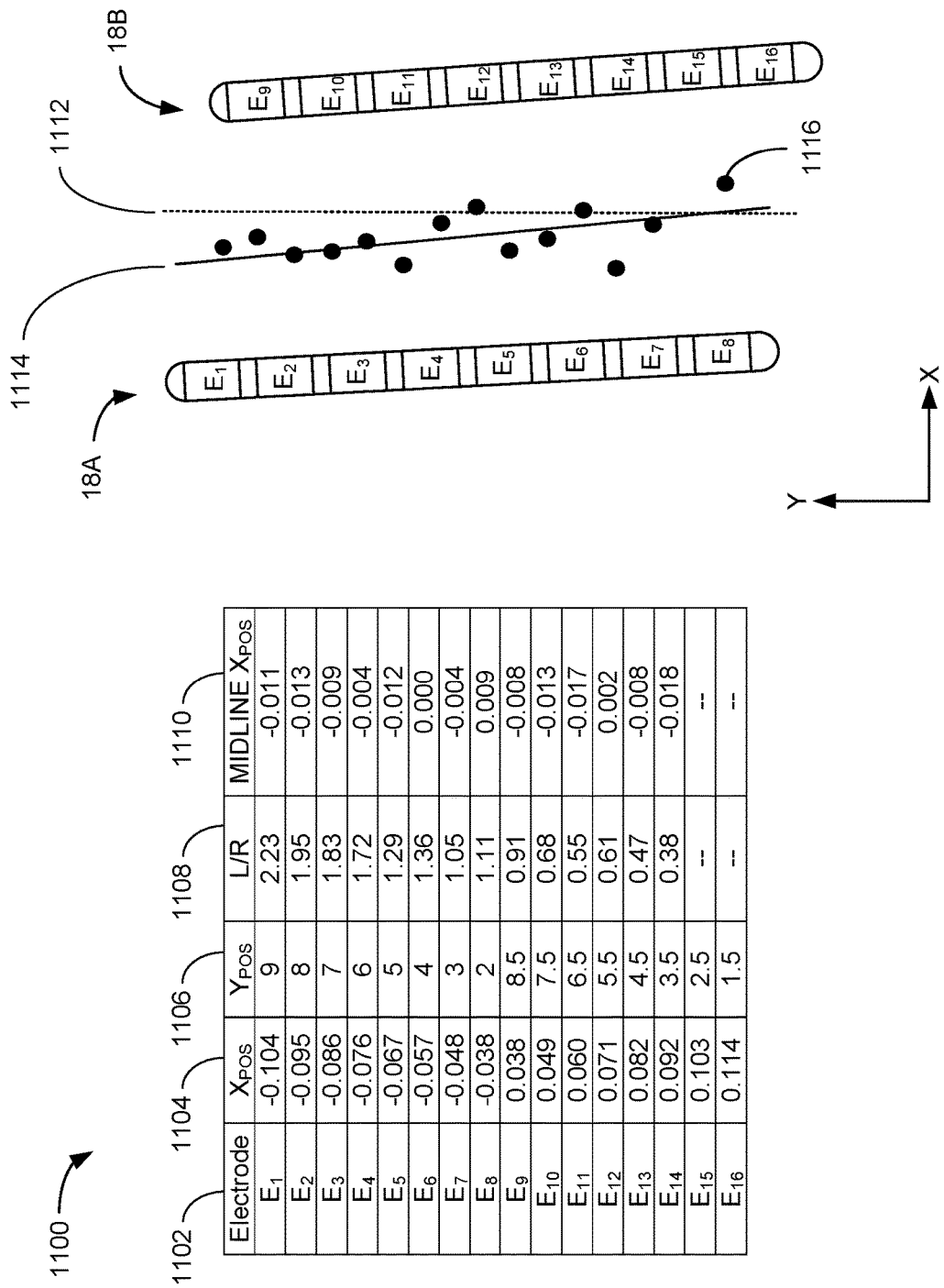
FIG. 11 shows an example data set and its use in determining the location of a physiological midline based on the peripheral monitoring physiological midline determination algorithm, in accordance with an example of the invention.

FIG. 11 illustrates an example data set 1100 associated with execution of the physiological midline algorithm 802 based on the example responses in FIG. 10. The data set 1100 includes an electrode identifier 1102, horizontal and vertical electrode positions 1104 and 1106, a measure of the electrode's position with respect to the physiological midline (expressed as response ratio 1108), and a midline horizontal position 1110. The horizontal and vertical positions of the electrodes 1104 and 1106 are determined, for example, based on the placement of a lead representation 506 over a fluoroscopic image 502 (FIG. 5), which establishes a spatial relationship of the spinal electrodes 16 that matches their actual positions. The coordinate system in the illustrated example employs a horizontal value of zero along an anatomical midline 1112, but the selection of a coordinate system is arbitrary. As shown, both electrode leads 18A and 18B have a slight slope with respect to the anatomical midline 1112.

The response ratio value 1108 (expressed as a left/right ratio) is based on the lateral responses of the peripheral electrodes 616 during execution of the algorithm 802 and quantifies the degree to which a spinal electrode is left or right of the physiological midline. Based on the expression of the ratio 1108 as a left/right ratio, a value of one indicates alignment with the physiological midline, a value of greater than one indicates a position (and the relative distance) left of the physiological midline, and a value of less than one indicates a position (and the relative distance) right of the physiological midline. While a left/right ratio 1108 is described, there are other ways in which the position and relative distance from the physiological midline may be expressed based on the responses measured at the peripheral electrodes as will be apparent to those of ordinary skill in the art.

The response ratio 1108 can be quantified in different ways. The left/right ratio 1108 may represent the sum of the quantified response values of all left side peripheral electrodes 616 over the sum of the quantified response values of all right side peripheral electrodes 616 during the stimulation of a particular spinal electrode 16. For example, the $E_1$ ratio may be calculated as the sum of the $L_1$ responses during the time periods $t_{1,1}$, $t_{1,2}$, and $t_{1,3}$ over the sum of the $R_1$ responses during the same time periods. In one embodiment, only those values that exceed the threshold may be included in the ratio calculation. The left/right ratio 1108 may, in another embodiment, represent the sum of the quantified response values of all left side peripheral electrodes 616 over the sum of the quantified response values of all right side peripheral electrodes 616 for only those corresponding pairs that exhibit a simultaneous bilateral response. That is, unilateral responses may be ignored in the calculation of the left/right ratio 1108. For example, the $E_1$ ratio may be calculated as the quantified $L_1$ response during the time period $t_{1,3}$ over the quantified $R_1$ response during the time period $t_{1,3}$. If an electrode (such as $E_{15}$ and $E_{16}$) does not cause a bilateral response at any stimulation amplitude, the electrode may not be considered in the computation of the physiological midline location. Alternatively, a spinal electrode that does not induce a bilateral response may be assigned a predetermined value (e.g., 3.0 for only left response and 0.33 for only right response). In the computation of the response ratio value, responses measured at different amplitude levels may also be weighted differently. For example, responses at lower amplitude stimulation levels may be given greater weight than responses at higher amplitude stimulation levels. While several examples have been given, it will be understood that the measure of a spinal electrode's position relative to the physiological midline may be expressed in many different additional ways.

The horizontal position of the physiological midline 1110 is calculated based on the response ratio 1108 and the known horizontal position of the corresponding spinal electrode 16. The first step in determining the horizontal midline position 1110 is relating the response ratio 1108 to a distance from the physiological midline. For example, $E_1$'s left/right ratio value of 2.23 indicates that it is the furthest left of the physiological midline of any electrode. However, this value must still be related to a distance from the physiological midline. In the illustrated embodiment, an electrode's left/right ratio value 1108 is multiplied by an initial correlation value, which is a predetermined value that approximates the relationship between the response ratio 1108 and the distance in the adopted coordinate system, and the resulting value is added to (or subtracted from if electrode is right of midline) the electrode's horizontal position value 1104. The calculated horizontal position of the physiological midline 1110 is utilized in conjunction with the electrode's vertical position as the electrode's contribution to the midline location. For example, electrode $E_1$'s left/right ratio value of 2.23 is multiplied by a correlation value of 0.042 to obtain a distance to midline value of 0.093, which is added to $E_1$'s horizontal position value of −0.104 to obtain the midline horizontal position of −0.011. The horizontal position of the physiological midline 1110 is utilized in conjunction with $E_1$'s vertical position of 9 to determine E1's contribution to the midline calculation—a point having a vertical position of 9 and a horizontal position of −0.011. The same calculation is repeated for each of the spinal electrodes 16 and the location of the physiological midline is determined based on the set of points 1116. For example, a linear regression may be performed using the set of points 1116 to determine the equation of the physiological midline 1114.

It will be understood that if the correlation value is not accurate, the resulting equation of the physiological midline 1114 may be flawed. For example, if the correlation value is too large, the calculated horizontal values will "overshoot" the physiological midline 1114. For example, electrodes left of the midline 1114 will contribute a data point that is right of the midline 1114 and vice versa. Likewise, if the correlation value is too small, the calculated horizontal values will "undershoot" the physiological midline 1114. In order to determine the ideal correlation value, the physiological midline location is performed as an iterative process. This may be accomplished by evaluating the "fit" of the computed physiological midline 1114 to the set of points 1116, adjusting the correlation value (in a direction dictated by whether there is an "overshoot" or "undershoot" error), and repeating the process. The process can be iteratively repeated until the equation of the physiological midline best "fits" the points 1116. This can be accomplished, for example, by identifying the correlation value that maximizes the coefficient of determination (i.e., the R squared value). Note that the points shown in FIG. 11 are based on a correlation value that is near the ideal value.

While the algorithm 802 has thus far been described in the context of stimulation between a single selected spinal electrode 16 and the corresponding electrode 620, "virtual" electrodes can also be created through the stimulation of combinations of spinal electrodes 16 (with or without the complementary electrode). The use of such virtual electrodes can provide additional stimulation locations that can be considered as part of the data set 1100, which can improve the results. Stimulation of multiple spinal electrodes 16 can occur within the same timing channel or using fractionalized pulses as described in U.S. Pat. No. 7,890,182, which is incorporated herein by reference. The stimulation location of a group of electrodes can be quantified in different ways. For example, the location of the electrical stimulation may be calculated as a centroid based upon the locations of the stimulating electrodes (which are known based on the placement of the representations 506, for example) weighted for the stimulation provided at the particular electrodes. For example, if $E_1$ and $E_9$ are simultaneously stimulated such that 40% of the cathodic current is applied to $E_1$ and 60% of the cathodic current is applied to $E_9$, the centroid of cathodic stimulation may be located at a point that is 60% of the distance between $E_1$ and $E_9$ away from $E_1$ along a line between the two electrodes. When stimulation current is sourced and sunk by spinal electrodes 16 (i.e., without corresponding electrode 620), the stimulation location may be defined as the centroid between a cathodic centroid and an anodic centroid or the combined centroid of all cathodic an anodic currents. The stimulation location of electrode combinations can also be quantified in other ways, and the results of such stimulation can be included in the data set 1100 (with the stimulation location identified by horizontal and vertical positions 1104 and 1106). The use of groups of stimulating electrodes can be used in the first instance to increase the size of the data set 1100 and can also be used to verify the results of the determined location of a physiological midline (e.g., by stimulating combinations of electrodes that result in a stimulation location that is at or near the calculated location of the physiological midline to verify the results).

Figure 12:
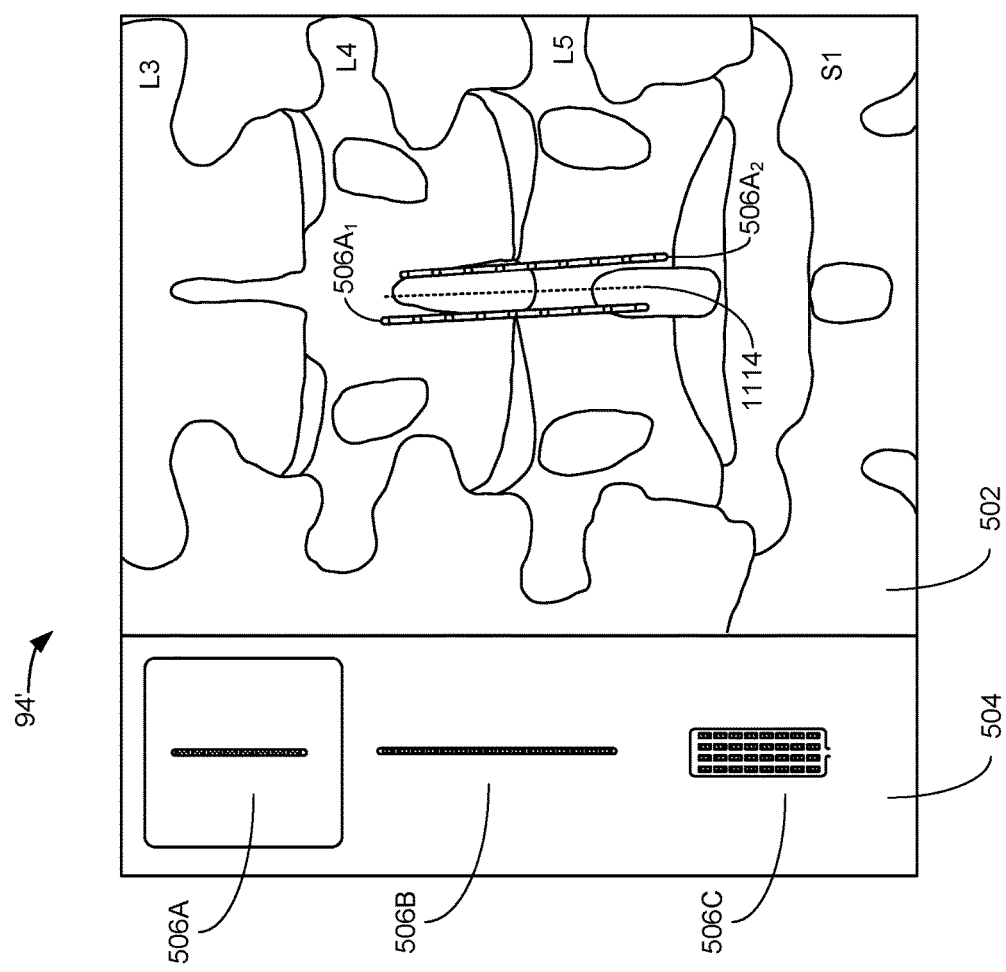
FIG. 12 shows an improved graphical user interface that includes the determined location of the physiological midline, in accordance with an example of the invention.

As illustrated in FIG. 12, the computed physiological midline 1114 can be displayed on the improved graphical user interface 94' in conjunction with the representations 506 and overlaying the image 502. As noted above, the physiological midline may not be aligned with an anatomical midline. Thus, the representation of the physiological midline 1114 (which can be displayed in conjunction with the illustration of a centroid of stimulation) provides a user with an additional piece of information in the determination of an appropriate stimulation program or in the evaluation of the suitability of the location of the implanted electrode leads.

Figure 13A:
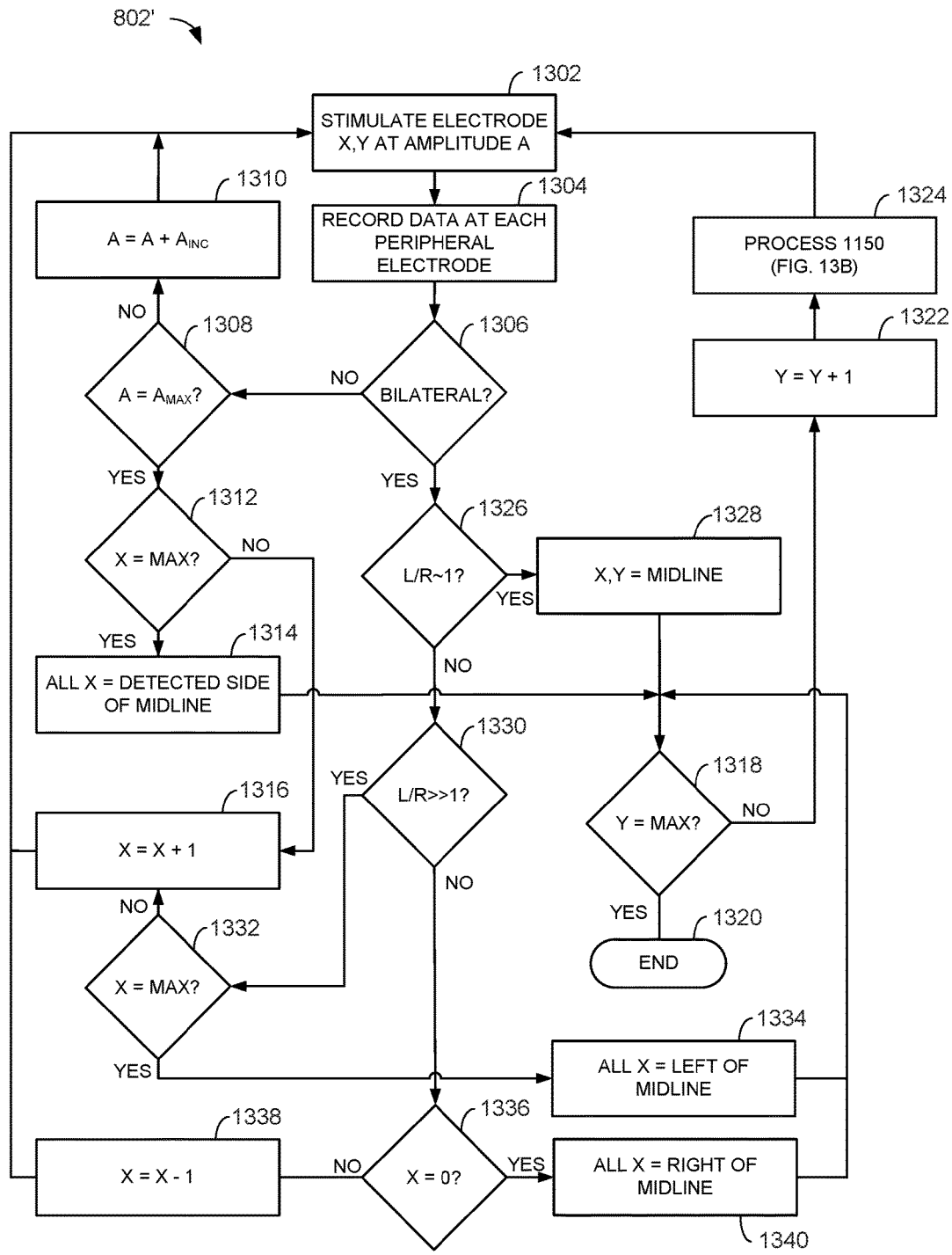
FIGS. 13A and 13B are flowcharts that show various steps of a modified peripheral monitoring physiological midline determination algorithm for use with an implanted paddle lead, in accordance with an example of the invention.

FIG. 13A illustrates the steps in a modified algorithm 802' that can be employed when the spinal electrodes 16 are positioned on a paddle lead (such as lead 60). The modified algorithm results in efficiency improvements (i.e., faster execution times) by identifying the location of the physiological midline laterally and then tracking it vertically, thereby avoiding the stimulation of many electrodes 16. For a paddle lead having X columns and Y rows, the column (X) and row (Y) values are set equal to one (which corresponds to the top left electrode position) and the amplitude (A) is set to the minimum amplitude ($A_{MIN}$). The selected electrode (X,Y) is then stimulated at the amplitude (A) (step 1302). The responses to stimulation are recorded at each of the peripheral electrodes (step 1304) and it is determined whether the stimulation resulted in a bilateral response (i.e., whether a super-threshold response was observed at each electrode in any corresponding pair of peripheral electrodes 616) (step 1306). If not (which indicates the response is either unilateral or that no response is observed), the amplitude is increased (if not already at the max value ($A_{MAX}$)) by the incremental value ($A_{INC}$) (step 1310) and stimulation is repeated at the same electrode and the increased amplitude (step 1302). If the amplitude is at the maximum value, the electrode position is shifted to the right by one column (step 1316) and stimulation continues at the new electrode and at the same amplitude (step 1302). If the stimulated electrode was in the far right column (i.e., the electrode position can't be shifted to the right) (step 1312), each electrode in the current row (Y) is assigned to the side of the midline on which a response was observed (i.e., the full row of electrodes is marked as left of the physiological midline if stimulation was observed on the left side and vice versa) (step 1314).

If a bilateral response is observed at step 1306, it is determined if the bilateral response ratio (such as left/right ratio 1108) is near a value of one (which indicates proximity to the physiological midline) (step 1326). If the response ratio is close to one (e.g., within a user-selectable range such as 0.8-1.2), the electrode position is marked as the physiological midline position (step 1328). If the response ratio is substantially greater than one (which indicates that the electrode is left of the physiological midline), the electrode position is shifted to the right by one column (step 1316) and the new electrode is stimulated at the current amplitude value (step 1302), or, if the stimulated electrode position is already in the far right column, the entire row is marked as left of the physiological midline (step 1334). If the response ratio is substantially less than one (which indicates that the electrode is right of the physiological midline), the electrode position is shifted to the left by one column (step 1338) and the new electrode is stimulated at the current amplitude value (step 1302), or, if the stimulated electrode position is already in the far left column, the entire row is marked as right of the physiological midline (step 1340).

Figure 13B:
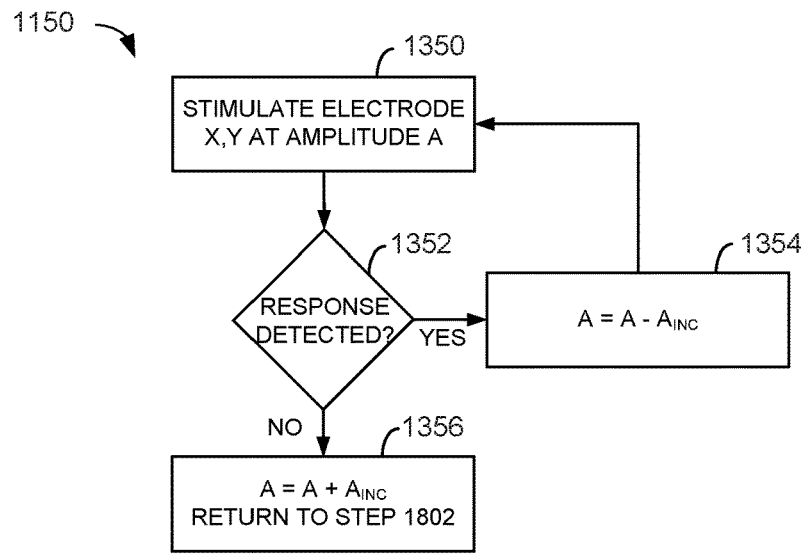

After the location of the physiological midline is identified within a row or it is determined that the entire row is on one side of the physiological midline (steps 1314, 1328, 1334, and 1340), if the selected electrode is in the bottom row (step 1318), the process concludes (step 1320). If the selected electrode is not in the bottom row, the electrode position is shifted down one row (step 1322) and the amplitude is adjusted (1324). As shown in FIG. 13B, the electrode at the new row is stimulated at the present amplitude value (step 1350) and it is determined if any response is detected (i.e., if there is a super-threshold response at any peripheral electrode) (step 1352). If any response is detected, the amplitude is decreased by the incremental amount (step 1354) and the electrode is again stimulated (step 1350). This process continues until no response is detected, at which point the amplitude is increased by the stimulation amount (step 1356) and the process flow returns to step 1302 (FIG. 13A). Although the process 802' has been described in the context of a starting point of the top left electrode and using a left/right response ratio, it will be understood that the process can be modified to use different starting points or expressions of the ratio value.

Figure 14A:
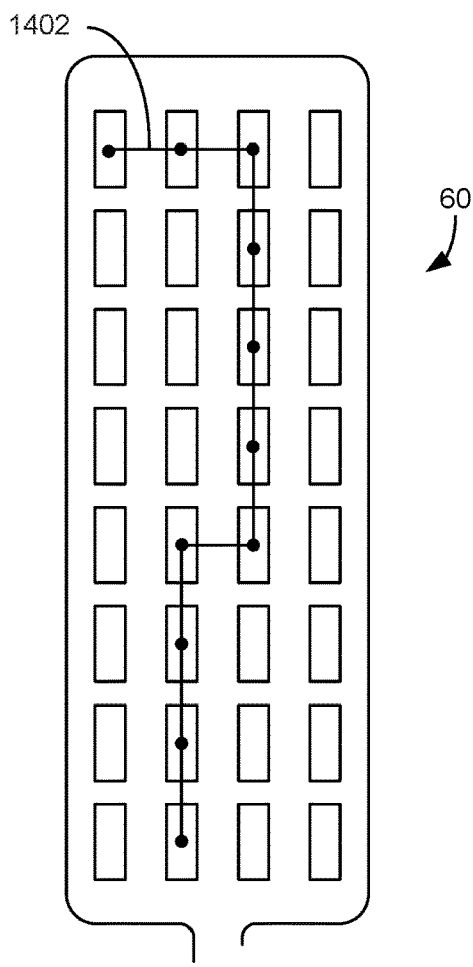
FIGS. 14A and 14B show a stimulation progression according to different variations of the algorithm described with respect to FIGS. 13A and 13B.
Figure 14B:
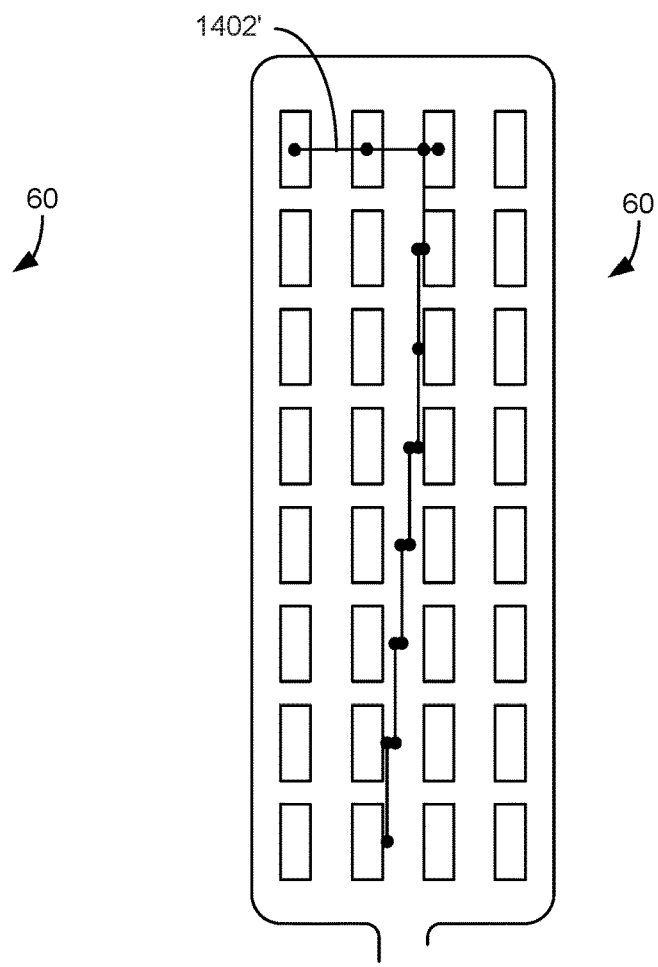

FIG. 14A shows an example flow 1402 (with each dot representing a stimulation point) through the process 802' for a paddle lead 60. As illustrated, the process 802' improves efficiency by identifying a midpoint laterally and then tracking the midpoint vertically through the rows of electrodes, thereby eliminating the need for stimulation of many of the electrodes. While the process 802' has been described in the context of an electrode-level resolution, it will be understood that the process 802' can be modified to utilize virtual electrodes to identify inter-electrode positions of the physiological midline as shown in FIG. 14B (path 1402') in a similar manner as described above with respect to the process 802. In such a modified approach, the lateral steps may be adjusted based on the response observed for stimulation at a particular position. For example, if stimulation results in a response ratio that is near one, a small lateral change of the stimulation location may be made. However, if stimulation results in a response ratio that is farther away from one, a larger lateral change of the stimulation location may be made.

Figure 15:
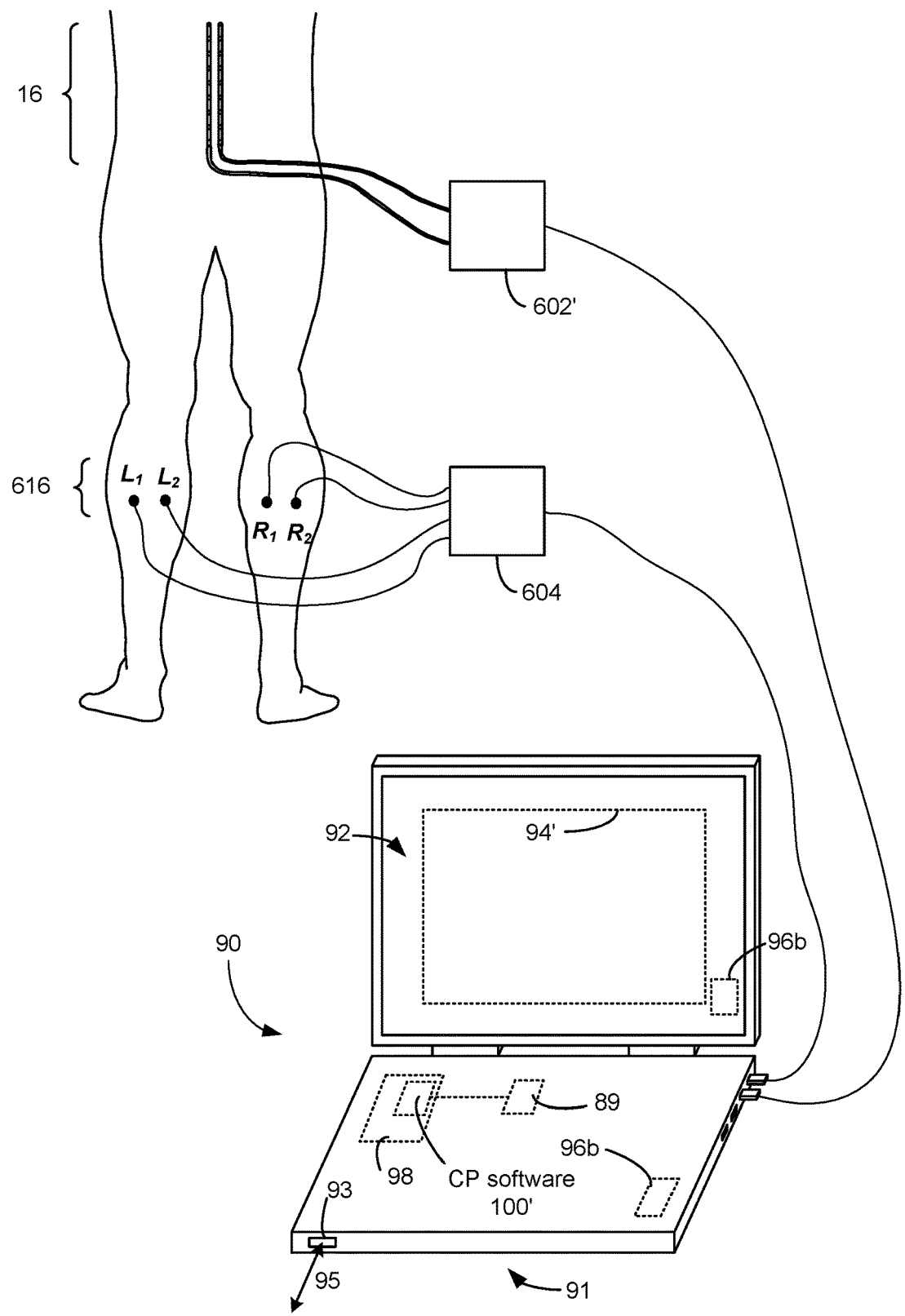
FIG. 15 shows the connection of a stimulating electrode device and a monitoring electrode device to a clinician's programmer system, in accordance with an example of the invention.

Referring to FIG. 15, a second aspect of the invention employs peripheral electrodes 616 as stimulating electrodes and spinal electrodes 16 as monitoring electrodes to determine the location of the physiological midline. The spinal electrode leads (two percutaneous leads 18 are shown) are electrically coupled to circuitry within a modified monitoring electrode device 602', which is modified from the device 602 in the sense that it may include a connector block similar to the connector block 22 to couple the individual electrodes 16 to the monitoring circuitry, and the peripheral electrodes 616 are connected to circuitry within a stimulating electrode device 604. The devices 602' and 604 are connected to the CP computer 91's USB ports 99; however, other wired or wireless connections can be employed as noted above. Because stimulation of a corresponding electrode ($E_C$) such as that utilized in the peripheral monitoring embodiment invokes the same type of response as stimulation at the peripheral electrodes 616, it is not utilized in the spinal monitoring embodiment. Instead, stimulation occurs between a pair of peripheral electrodes 616 located on the same side of the body, such as $L_1$ and $L_2$ or $R_1$ and $R_2$. While the pairs of peripheral electrodes 616 are illustrated as being in close proximity to one another, stimulating pairs may also include remote electrodes that are located on the same side of the body. Because the technique is based upon relative responses of the spinal electrodes to stimulation on each side of the body, it is preferred that a pair of stimulating peripheral electrodes 616 on one side of the body is mirrored by a corresponding pair on the other side of the body. While two corresponding pairs of stimulating peripheral electrodes are illustrated, additional pairs may also be employed. Moreover, peripheral electrodes on the same side of the body may be used in different paired combinations.

Figure 16:
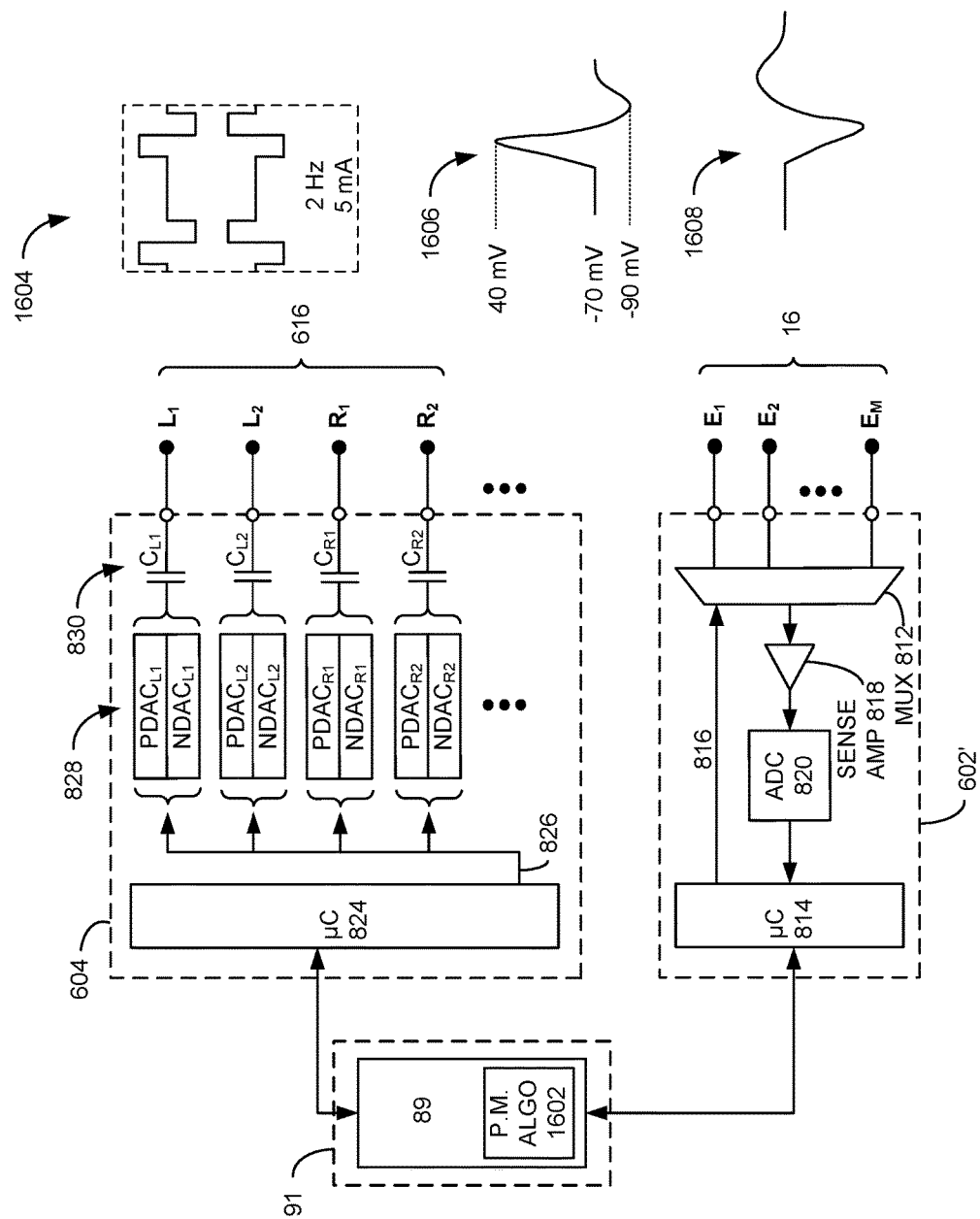
FIG. 16 shows a portion of the circuitry of the stimulating electrode device, the monitoring electrode device, and the clinician's programmer along with example stimulation patterns and induced responses associated with a spinal monitoring physiological midline determination, in accordance with an example of the invention.

As shown in FIG. 16, the connection of the CP computer 91 to the devices 604 and 602' and the internal circuitry of such devices is substantially the same as described above with respect to the peripheral monitoring embodiment (FIG. 8), with the exception that the stimulation circuitry is coupled to the peripheral electrodes 616 and the monitoring circuitry is coupled to the spinal electrodes 16. Therefore, a repetitive description of such interconnections and circuitry is omitted.

The spinal monitoring physiological midline algorithm 1602 executed by the CP computer 91 operates on the principle that stimulation of selected peripheral electrodes 616 (such as with the stimulation pattern 1604 illustrated for electrodes $L_1$ and $L_2$) causes sensory neurons to "fire," which results in changes in the neurons' membrane potential over a short period of time, causing the propagation of an electrical signal towards the brain. An example of this response, called an action potential, is illustrated at 1606 from the perspective of the inside of a neuron. As shown, in a resting state, the inside of the neuron's membrane is at a negative potential (on the order of −70mV) with respect to the outside of the membrane. As the neuron "fires," the membrane potential rapidly increases (depolarizes) to a maximum amplitude (on the order of 40mV) and then rapidly decreases (repolarizes) past the resting potential to a minimum amplitude (on the order of −90mV) before settling back to the resting potential. Neurons can be caused to "fire" by the application of electrical stimulation such as the stimulation of the peripheral electrodes $L_1$ and $L_2$ shown at 1604. The induced response propagates through a chain of neurons at a rate of approximately 40 to 100 meters per second through nerve fibers on the same side of the body as the stimulation point into the spinal column and to the brain. Thus, at a certain time after the stimulation (based on the propagation rate), electrodes positioned along spinal nerves (e.g., spinal electrodes 16) observe the propagating signal (called an evoked compound action potential, or ECAP) as a response such as that illustrated at 1608, which represents the combined electrical effect of numerous neurons undergoing the transition illustrated at 1606. Note that the observed response is inverted from the response shown at 1606 because an increasing potential inside of a nerve cell is observed as a decreasing potential by an electrode outside of such a cell and vice versa. Because there is a lateral nature to the propagation of action potentials, a spinal electrode 16 positioned closer to the side of the body on which stimulation occurs (i.e., on the same side of the physiological midline) will experience a greater response than an electrode on an opposite side of the physiological midline. Therefore, the responses of the spinal electrodes 16 to peripheral stimulation at different lateral positions can be analyzed to determine their positions with respect to the physiological midline. Note that the peripheral electrodes 616 must be positioned in a location such that stimulation induces a signal that propagates past the location of the spinal electrodes 16. For example, spinal electrodes placed in the lower back (i.e., proximate to the lumbar and/or sacral nerves) would not observe an ECAP signal caused by stimulation on an arm because such a signal would propagate through a spinal nerve towards the brain (i.e., "downstream") from the spinal electrodes 16.

Figure 17:
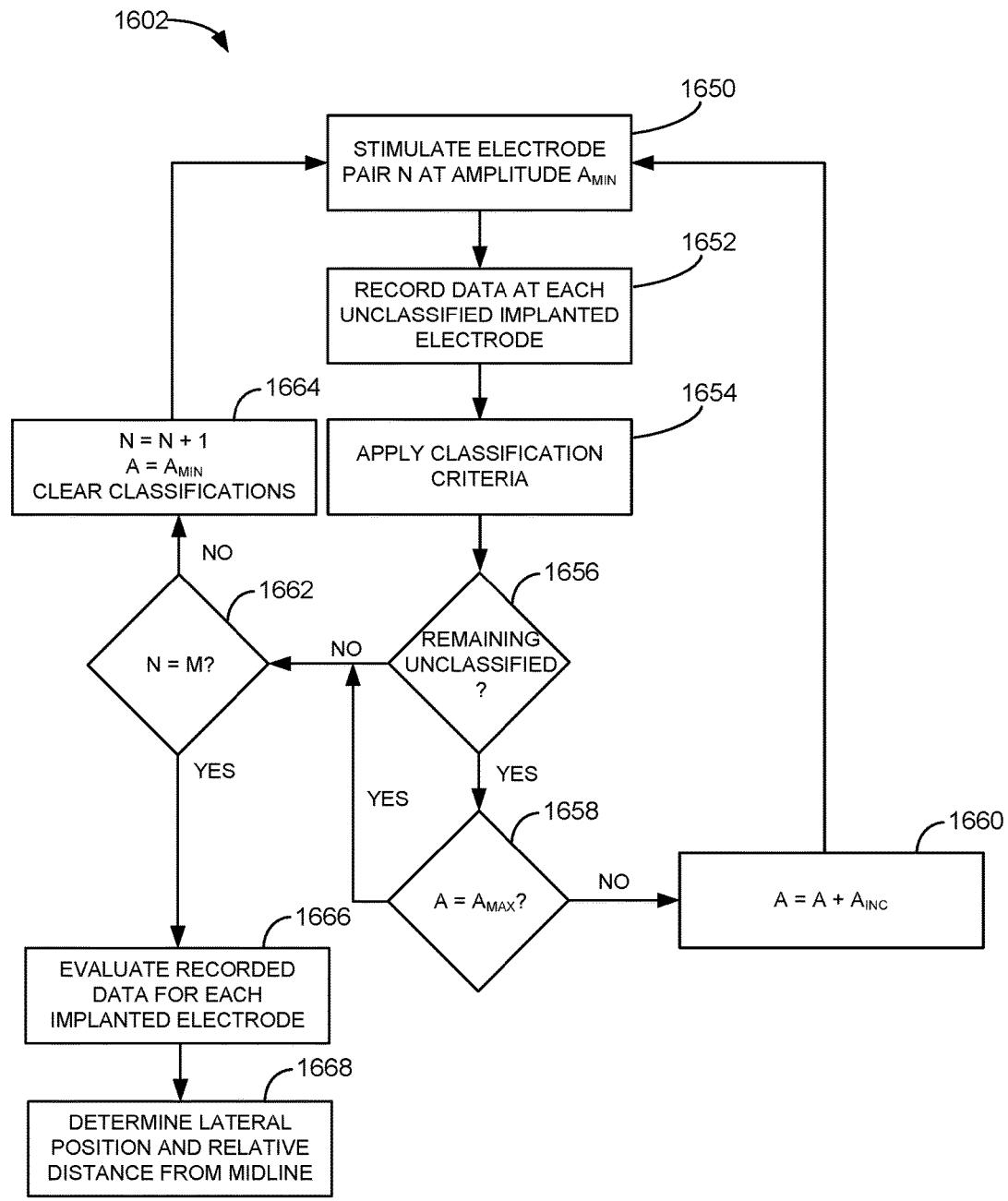
FIG. 17 is a flowchart that shows various steps of a spinal monitoring physiological midline determination algorithm, in accordance with an example of the invention.

The steps of an example spinal monitoring physiological midline algorithm 1602 are illustrated in flowchart form in FIG. 17. Initially, a selected pair (N) of peripheral electrodes 616 (such as $L_1$ and $L_2$, for example) is stimulated at a minimum amplitude ($A_{MIN}$), which may be a customizable parameter of the algorithm 1602 (step 1650). The peripheral electrodes 616 may be either surface electrodes or electrodes inserted through the skin into contact with a muscle or nerve. Note that the amplitude level required to evoke the ECAP response is far lower than the amplitude required to recruit motor neurons, so the minimum amplitude may be less in the spinal monitoring embodiment than in the peripheral monitoring embodiment. In one embodiment, the electrodes in the selected pair are stimulated using a square waveform having a low frequency of approximately 2-10 Hz and opposite polarities. However, the desired stimulation parameters may be user-selectable.

During stimulation, the ECAP response at each of the unclassified spinal electrodes 16 is recorded (step 1652). As described below, spinal electrodes 16 are "classified" when enough information has been collected regarding the particular spinal electrode 16 for a selected stimulation pair such that no additional information needs to be recorded. The ECAP signals observed by the spinal electrodes 16 may be recorded serially (via multiplexer 812, for example) or in parallel if dedicated sense amps 818 and ADCs 820 are provided for each electrode. Because an ECAP signal is propagated for each stimulation pulse, data may be recorded for each electrode 16 over a duration that spans multiple pulses in order to capture multiple ECAP signals. Such recording may involve the storage in memory (either in CP system 90 or monitoring electrode device 602') of the digitized values of the signals.

Classification criteria are then applied (step 1654) to the recorded data to determine whether any additional spinal electrodes 16 can be classified. The classification criteria serve to avoid the recordation of additional data related to electrodes for which sufficient data has been collected for the selected stimulating pair. The classification criteria may be analogous to those employed in the spinal stimulation embodiment may be avoided for electrodes that have observed a response to stimulation of the pair of electrodes at a certain number of amplitude levels or for electrodes that have observed a response to corresponding bilateral pairs of stimulating electrodes. Other classification criteria may be employed and, in one embodiment, may be user-programmable. While the application of classification criteria may decrease the execution time of the algorithm 1602, especially where serial processing of the spinal electrode signals is employed, their use is not strictly necessary and may be omitted. As described above with respect to the algorithm 802, some processing of the recorded data will be required at the recording step in order to apply the classification criteria.

After the classification criteria have been applied, it is determined whether any remaining unclassified spinal electrodes 16 exist (step 1656). If there are still unclassified electrodes 16, it is determined whether the amplitude (A) is equal to the maximum amplitude ($A_{MAX}$) (step 1658). If the amplitude is not equal to the maximum amplitude, it is increased by the incremental value ($A_{INC}$) (step 1660), which may be user-programmable, and the selected pair of electrodes is stimulated at the increased amplitude value (step 1650). If, however, there are no remaining unclassified electrodes 16 or the amplitude is equal to the maximum amplitude, it is determined whether the pair of electrodes 616 is the last pair (M) (step 1662). If not, the next pair of peripheral electrodes is selected, the amplitude is set equal to the minimum amplitude, the classifications are cleared (step 1664), and the new pair of electrodes is stimulated (step 1650).

Once the process has proceeded through all of the stimulating pairs, the recorded data is evaluated for each of the spinal electrodes 16 (step 1666) and the lateral position (i.e., left or right of physiological midline) and relative distance from the physiological midline is determined for each electrode (step 1668). These steps are best described with reference to FIG. 18.

Figure 18:
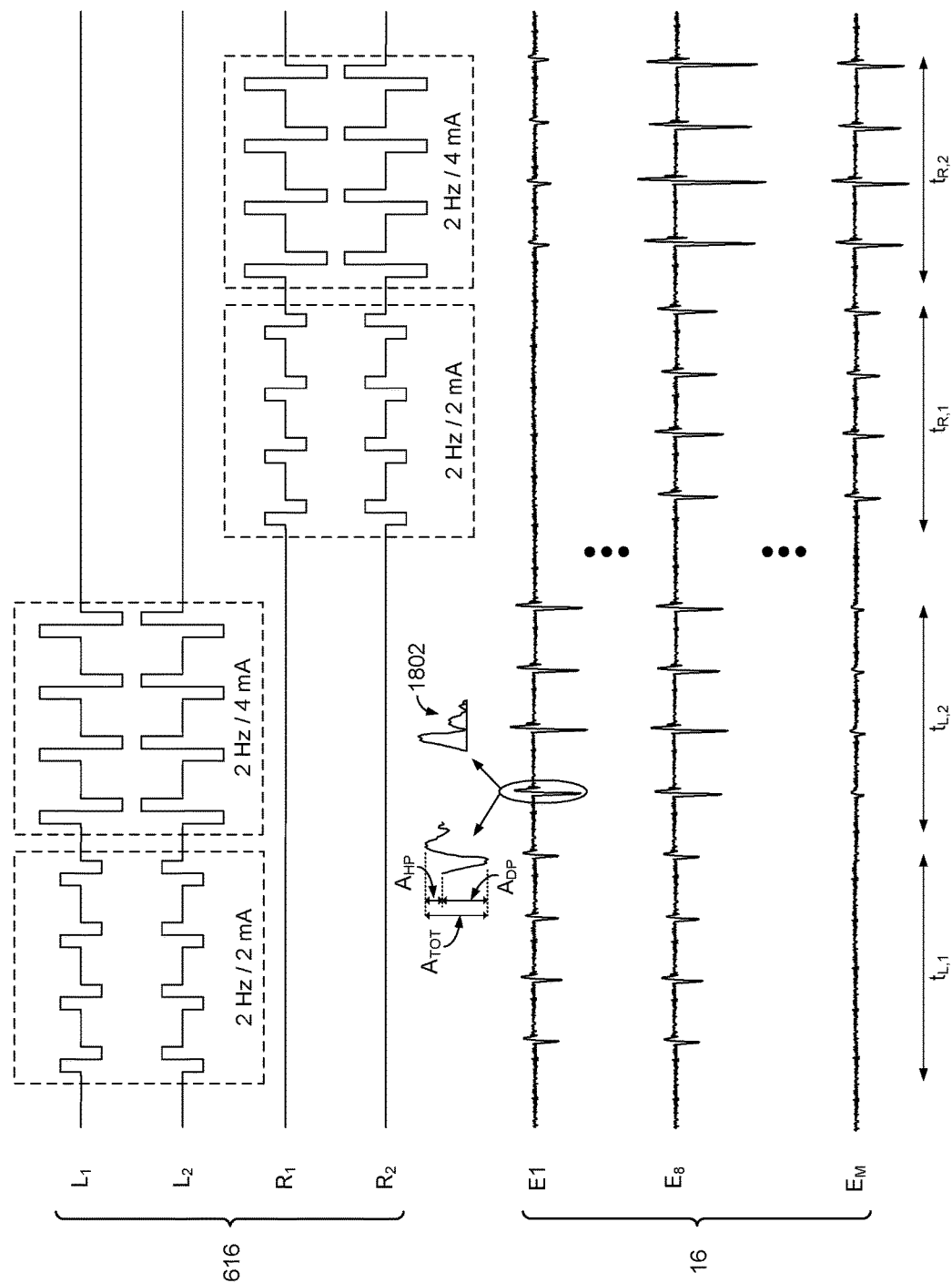
FIG. 18 shows example stimulation patterns and response signals associated with the spinal monitoring physiological midline determination algorithm, in accordance with an example of the invention.

FIG. 18 illustrates the stimulation patterns of various peripheral electrodes 616 and the response at various spinal electrodes 16 in an example execution of the algorithm 1602 and based on similar spinal electrode positions to the example in FIG. 10. As in FIG. 10, only a limited number of stimulating electrodes are shown and the incremental increase in stimulation amplitude between stimulation cycles is exaggerated for purposes of illustration. Electrodes $L_1$ and $L_2$ (inserted in a patient's left leg, for example) are initially stimulated using a square waveform at a frequency of 2 Hz and an amplitude of 2 mA (opposite polarities) during a time period $t_{L,1}$. Each pulse during the time period $t_{L,1}$ results in a super-threshold ECAP response at the $E_1$ and $E_8$ electrodes and a sub-threshold ECAP response at the $E_M$ electrode. As illustrated, the observed ECAP signals each follow a stimulation pulse by a duration that is based on the propagation speed of the ECAP signal from the point of stimulation to the point of detection. During time period $t_{L,2}$, the $L_1$ and $L_2$ electrodes are stimulated at an increased amplitude of 4 mA, which results in ECAP responses at electrodes $E_1$ and $E_8$ that have increased magnitudes as compared to those observed during $t_{L,1}$ as well as relatively small ECAP responses at $E_M$.

Electrodes $R_1$ and $R_2$ (inserted in a patient's right leg, for example) are thereafter stimulated using a square waveform at a frequency of 2 Hz and an amplitude of 2 mA (opposite polarities) during a time period $t_{R,1}$. The stimulation during $t_{R,1}$ results in super-threshold ECAP responses at the $E_8$ and $E_M$ electrodes and a sub-threshold ECAP response at the $E_1$ electrode. During time period $t_{R,2}$, the $R_1$ and $R_2$ electrodes are stimulated at an increased amplitude of 4 mA, which results in ECAP responses at electrodes $E_8$ and $E_M$ that have increased magnitudes as compared to those observed during $t_{R,1}$ as well as relatively small ECAP responses at electrode $E_1$. Although the ECAP responses are shown for all of the example electrodes ($E_1$, $E_8$, and $E_M$) for each stimulation sequence, it will be understood that the responses may not be recorded simultaneously (e.g., responses may be recorded one electrode at a time via the multiplexer 812) and that some responses may not be recorded at all based on the satisfaction of classification criteria. Therefore, the length of a stimulation sequence (although shown as a brief period) may be determined based on the number of electrodes 16 for which responses are to be recorded and the manner in which recording occurs (i.e., serially or in parallel).

The ECAP responses can be quantified in different manners. For example, an ECAP response can be quantified based on the amplitude of its hyperpolarization phase ($A_{HP}$), the amplitude of its depolarization phase ($A_{DP}$), or the sum of those values ($A_{TOT}$). Alternatively, the ECAP signal may be rectified as shown at 1802 and quantified based on its integral. It will be understood that quantification may depend on the time at which the ECAP signal is determined to start and stop, which may be determined as a function of the stimulation pulse timing.

Based on the quantified ECAP values, a measure of each spinal electrode's relative position with respect to the physiological midline, such as the left/right ratio value 1108, can be calculated in ways that are analogous to those described above with respect to the peripheral monitoring embodiment. For a particular spinal electrode 16, the left/right ratio 1108 may represent the sum of the quantified ECAP response values induced by stimulation of all left side peripheral electrode pairs (e.g., $L_1$ and $L_2$) over the sum of the quantified ECAP response values induced by stimulation of all right side peripheral electrode pairs (e.g., $R_1$ and $R_2$). For example, the E1 ratio may be calculated as the sum of all quantified ECAP responses for $E_1$ during $t_{L,1}$ and $t_{L,2}$ over the sum of all quantified ECAP responses for $E_1$ during $t_{R,1}$, and $t_{R,2}$. In another embodiment, the ratio value 1108 may ignore ECAP response values for which no response was measured for the corresponding pair of peripheral electrodes 616 at the corresponding amplitude (i.e., the ratio value may only incorporate bilateral responses). For example, for $E_1$, only the responses during $t_{L,2}$ and $t_{R,2}$ (along with other bilateral $E_1$ responses that are induced by other corresponding stimulating pairs) are included in the ratio 1108 calculation. A spinal electrode that does not exhibit any bilateral response may be either excluded from the physiological midline calculation or assigned a predetermined ratio 1108 (e.g., 3.0 for only left response and 0.33 for only right response). As described above, responses measured at different amplitude levels may also be weighted differently in the calculation of the ratio value 1108. These are just a few of the ways in which the quantified ECAP responses can be quantified into a measure of a spinal electrode 16's position relative to the physiological midline and numerous others will be apparent to those of skill in the art.

Having determined a measure of various spinal electrodes' positions relative to a physiological midline such as ratio 1108 or a similar value, the location of the physiological midline can be computed in the same way as described above with respect to FIG. 11. That is, the known spinal electrode positions can be utilized in conjunction with the measures of the electrodes' positions relative to the physiological midline to compute locations along the physiological midline. As described above, the location of the physiological midline may be determined using an iterative process, and, once determined, may be presented on a user interface 94' such as the one shown in FIG. 12. In one embodiment, the spinal monitoring embodiment and the peripheral monitoring embodiment may be utilized in combination to obtain a more accurate position of the physiological midline. For example, different measures of a spinal electrode 16's position relative to the physiological midline (e.g., ratio values 1108) may be determined from the spinal monitoring and peripheral monitoring processes and used in combination to compute the location of the physiological midline. Similarly, the physiological midline location might be determined using the spinal monitoring process and then verified using the peripheral monitoring process (e.g., by stimulating combinations of electrodes that result in a stimulation location that is on or near the physiological midline location determined using the spinal monitoring process).

Figure 19:
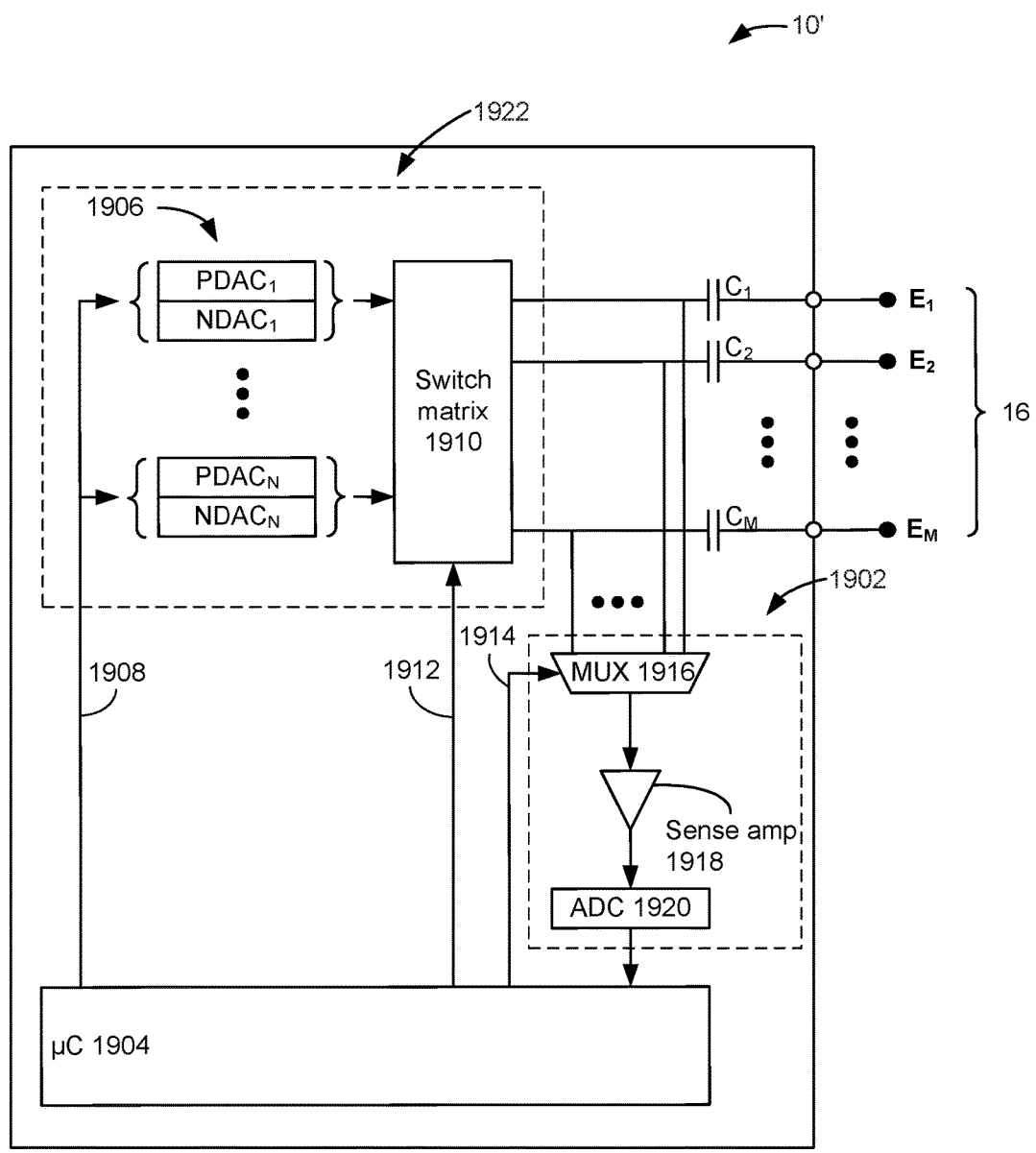
FIG. 19 shows a portion of the circuitry of a modified IPG that can be used for both stimulating and sensing spinal electrodes, in accordance with an example of the invention.

Although the physiological midline determination process has been described in the context of its use prior to full implantation of an IPG 10, the process can also be utilized after implantation. As illustrated in FIG. 19, in order to enable the use of the spinal monitoring process with a fully implanted stimulator, the circuitry of a modified IPG 10' may be adapted to include sense circuitry 1902 (which mirrors the circuitry within the monitoring device 602, 602') such that ECAP responses can be recorded from the electrodes 16. When used in a stimulation mode, a microprocessor 1904 in the IPG 10' may deliver stimulation parameters as digital signals to one or more DACs 1906 over the bus 1908, map the output of the one or more DACs to the desired electrode(s) 16 via control signals to the switch matrix 1910 over the bus 1912, and issue control signals over the bus 1914 to the multiplexer 1916 to decouple the electrodes from the remainder of the sense circuitry 1902 (i.e., from sense amp 1918 and ADC 1920). When the peripheral monitoring process is executed using the IPG 10', the IPG's case 12 may serve as the corresponding electrode ($E_C$). Alternatively, an external stimulation device that is synchronized with the IPG 10' by the CP system 90 may be utilized to stimulate an external corresponding electrode. When used in a sense mode, the microprocessor 1904 may decouple the electrodes 16 from the stimulation circuitry 1922 via control signals to the switch matrix 1910 and route the signals from the selected electrodes 16 (such as ECAP signals caused by peripheral stimulation) to the sense amp 1918 and ADC 1920 via control signals to the multiplexer 1916. The digitized response signals from the ADC 1920 may be processed to some extent by the microprocessor 1904 or passed to the CP system 90 in raw form. The IPG 10' may be responsive to stimulation or data retrieval commands (depending on whether the spinal monitoring or peripheral monitoring process is selected) issued by the CP system 90. Commands and data may be communicated between the CP system 90 and the IPG 10' wirelessly using communication circuitry described above. While the physiological midline determination algorithms have been described in the context of their execution on the CP computer 91, the algorithms could also be executed on the external controller 40.

While the invention herein disclosed has been described by means of specific embodiments and applications thereof, numerous modifications and variations could be made thereto by those skilled in the art without departing from the scope of the invention set forth in the claims.

What is claimed is:

1. A non-transitory computer-readable medium, comprising instructions to cause control circuitry to:
send instructions to a stimulation device to provide electrical stimulation at one or more stimulation amplitudes at each of a plurality of spinal electrodes that are implantable in a patient;
receive data that is indicative of a response to the electrical stimulation at each of one or more corresponding pairs of peripheral electrodes, wherein each pair of peripheral electrodes comprises electrodes that are positionable on different sides of the patient's body;
calculate, based on the received data, a measure of a relative position of the plurality of spinal electrodes to a physiological midline; and
calculate, based on the measure of the relative position and a vertical and horizontal location of each of the plurality of spinal electrodes, the location of the physiological midline.

2. The computer-readable medium of claim 1, further comprising instructions to cause the control circuitry to display the location of the physiological midline on a graphical user interface.

3. The computer-readable medium of claim 1, further comprising instructions to cause the control circuitry to determine the vertical and horizontal location of each of the plurality of spinal electrodes.

4. The computer-readable medium of claim 3, wherein the instructions to determine the location of each of the plurality of spinal electrodes comprise instructions to determine the location of each of the plurality of spinal electrodes based on a position of a representation of the electrodes in a graphical user interface.

5. The computer-readable medium of claim 1, wherein the stimulation device is an external trial stimulator.

6. The computer-readable medium of claim 1, wherein the stimulation device is an implantable pulse generator.

7. The computer-readable medium of claim 1, wherein the instructions to the stimulation device comprise instructions to provide electrical stimulation at a complementary electrode that is affixable to the patient's skin.

8. The computer-readable medium of claim 1, wherein the instructions to the stimulation device comprise instructions to provide electrical stimulation at each of the plurality of spinal electrodes independently.

9. The computer-readable medium of claim 1, wherein the instructions to the stimulation device comprise instructions to proceed sequentially through the plurality of spinal electrodes.

10. The computer-readable medium of claim 1, wherein the instructions to receive data that is indicative of a response to the electrical stimulation comprise instructions to request the data from a device to which the one or more corresponding pairs of peripheral electrodes are coupled.

11. The computer-readable medium of claim 1, wherein the one or more corresponding pairs of peripheral electrodes are electromyography electrodes.

12. The computer-readable medium of claim 1, wherein the instructions to calculate the measure of the relative position of each of the plurality of spinal electrodes comprise instructions to calculate the measure of the relative position as a ratio of the response at a first electrode in one of the corresponding pairs to the response at a second electrode in the one of the corresponding pairs to stimulation at the spinal electrodes.

13. The computer-readable medium of claim 1, wherein the instructions to calculate the location of the physiological midline comprise instructions to iteratively adjust a correlation value that relates the measure of the relative position to a distance from the physiological midline.

14. The computer-readable medium of claim 1, wherein the instructions to calculate the location of the physiological midline comprise instructions to perform a linear regression on physiological midline location data point contributions related to at least some of the spinal electrodes.

15. A system, comprising:
a display;
a memory; and
control circuitry configured to execute program code stored in the memory to cause the control circuitry to:
send instructions to a stimulation device to provide electrical stimulation at one or more stimulation amplitudes at each of a plurality of spinal electrodes that are implantable in a patient;
receive data that is indicative of a response to the electrical stimulation at each of one or more corresponding pairs of peripheral electrodes, wherein each pair of peripheral electrodes comprises electrodes that are positionable on different sides of the patient's body;
calculate, based on the received data, a measure of a relative position of the plurality of spinal electrodes to a physiological midline; and
calculate, based on the measure of the relative position and a vertical and horizontal location of each of the plurality of spinal electrodes, the location of the physiological midline.

16. The system of claim 15, further comprising program code to cause the control circuitry to display the location of the physiological midline on a graphical user interface.

17. The system of claim 16, wherein the program code to display the location of the physiological midline on the graphical user interface comprises program code to display the physiological midline over an anatomical image.

18. The system of claim 15, wherein the stimulation device is an external trial stimulator.

19. The system of claim 15, wherein the stimulation device is an implantable pulse generator.

20. The system of claim 15, wherein the program code to calculate the measure of the relative position of each of the plurality of spinal electrodes comprises program code to calculate the measure of the relative position as a ratio of the response at a first electrode in one of the corresponding pairs to the response at a second electrode in the one of the corresponding pairs to stimulation at the spinal electrodes.

* * * * *